(12) United States Patent
Lanes et al.

(10) Patent No.: US 7,037,703 B2
(45) Date of Patent: May 2, 2006

(54) COD URACIL-DNA GLYCOSYLASE, GENE CODING THEREFORE, RECOMBINANT DNA CONTAINING SAID GENE OR OPERATIVE PARTS THEREOF, A METHOD FOR PREPARING SAID PROTEIN AND THE USE OF SAID PROTEIN OR SAID OPERATIVE PARTS THEREOF IN MONITORING OR CONTROLLING PCR

(75) Inventors: Olav Lanes, Tromso (NO); Nils Peder Willasen, Tromsö (NO); Per Henrik Guddal, Drangedal (NO); Dag Rune Gjellesvik, Tromsö (NO)

(73) Assignee: Biotec Pharmacon ASA, Tromso (NO)

( * ) Notice: Subject to any disclaimer, the term of this patent is extended or adjusted under 35 U.S.C. 154(b) by 0 days.

(21) Appl. No.: 09/758,017

(22) Filed: Jan. 10, 2001

(65) Prior Publication Data

US 2002/0155573 A1 Oct. 24, 2002

(30) Foreign Application Priority Data

Jan. 12, 2000 (NO) ............................................ 20000163
Jan. 25, 2001 (NO) ............................................ 20005428

(51) Int. Cl.
*C12N 9/24* (2006.01)
*C12P 19/34* (2006.01)
*C07H 21/04* (2006.01)

(52) U.S. Cl. ...................... 435/200; 435/91.2; 536/23.2
(58) Field of Classification Search .................. 435/200, 435/91.2; 536/23.2
See application file for complete search history.

(56) References Cited

FOREIGN PATENT DOCUMENTS

WO 9720922 6/1997
WO 9725416 7/1997

OTHER PUBLICATIONS

Lanes et al. Comparative Biochemistry and physiology Part B (Nov. 2000), vol. 127, pp. 399–410.*
Lanes et al. (2002) Extremophiles, vol. 6, pp. 73–86.*
Lindahl, T., *An N-glycosidase from Escherichia coli that releases free uracil from DNA containing deaminated cytosine residues.* Proc. Natl. Acad. Sci., (1974), 71(9): pp 3649–3653.
Kubota, Y., et al. *Reconstitution of DNA base excision-repair with purified human proteins; interaction between polymerase beta and the XRCC1 protein.* Embo J. (1996), 15(23): pp 6662–6670.
Nicholl, I.D., K. Nealon, and M.K. Kenny. *Reconstitution of human base excision repair with purified proteins.* Biochemistry (1997), 36(24): pp 7557–7566.

Parikh, S.S., C.D. Mol, and J.A. Tainer. *Base excision repair enzyme family portrait: integrating the structure and chemistry of an entire DNA repair pathway.* Structure (1997), 5(12): pp 1543–1550.
Slupphaug, G., et al. *Cell cycle regulation and in vitro hybrid arrest analysis of the major human uracil–DNA glycosylase.* Nucleic Acids Res., (1991), 19(19): pp 5131–5137.
Muller, S.J. and S. Caradonna. *Isolation and characterization of a human cDNA encoding uracil–DNA glycosylase.* Biochim. Biophys. Acta., (1991), 1088(2): pp 197–207.
Muller Weeks, S.J. and S. Caradonna. *Specific association of cyclin–like uracil–DNA glycosylase with the proliferating cell nuclear antigen.* Exp. Cell. Res., (1996). 226(2): pp 346–355.
Haushalter, K.A., et al. *Identification of a new uracil–DNA glycosylase family by expression cloning using synthetic inhibitors.* Curr. Biol., (1999), 9(4): pp 174–185.
Gallineri, P. and J. Jiricny, *A new class of uracil–DNA glycosylases related to human thymine –DNA glycosylase.* Nature, (1996), 383(6602): pp 735–738.
Barrett, T.E., et al. *Crystal structure of a G:T/U mismatch-specific DNA glycosylase: mismatch recognition by complementary–strand interactions.* Cell, (1998), 92(1): pp 117–129.
Sandigursky, M. and W.A. Franklin. *Thermostable uracil–DNA glycosylase from Thermotoga maritima a member of a novel class of DNA repair enzymes,* Curr. Biol., (1999), 9(10): pp 531–534.
Krokan, H.E., R. Standal, and G. Slupphaug, *DNA glycosylases in the base excision repair of DNA.* Biochem. J., (1997), 325(Pt. 1): pp 1–16.
Higley, M. and R.S. Lloyd, *Processivity of uracil DNA glycosylase.* Mutat. Res., (1993), 294(2): pp 109–116.
Bennett, S.E., R.J. Sanderson, and D.W. Mosbaugh, *Processivity of Escherichia coli and rat liver mitochondrial uracil–DNA glycosylase is affected by NaCl concentration,* Biochemistry, (1995), 34(18): pp 6109–6119.
Purmal, A.A., et al. *Uracil DNA N–glycosylase distributively interacts with duplex polynucleotides containing repeating units of either TGGCCAAGCU or TGGCCAAGCTTGGCCAAGCU,* J.Biol. Chem., (1994), 269(35): pp 22046–22053.
Colson, P. and W.G. Verly, *Intracellular localization of rat–liver uracil–DNA glycosylase. Purification and properties of the chromatin enzyme,* Eur.J. Biochem, (1983), 134(3): pp 415–420.

(Continued)

*Primary Examiner*—Elizabeth Slobodyansky
(74) *Attorney, Agent, or Firm*—Ladas & Parry LLP

(57) ABSTRACT

It is disclosed a novel enzyme present in cod liver, a DNA sequence encoding the enzyme or operative parts or biologically functional parts thereof, a novel recombinant DNA comprising the gene or the operative or biologically functional parts thereof, a method of preparing the enzyme from cod liver and from bacteria carrying the gene, the bacteria carrying the gene per se, and the use of the protein in monitoring and/or controlling PCR or related reaction systems.

6 Claims, 7 Drawing Sheets

U.S. PATENT DOCUMENTS

Domena, J.D. and D.W. Mosbaugh, *Purification of nuclear and mitochondrial uracil–DNA glycosylase from rat liver. Identification of two distinct subcellular forms.* Biochem., (1985), 24(25): pp 7320–7328.

Domena, J.D., et al. *Purification and properties of mitochondrial uracil–DNA glycosylase from rat liver*, Biochem., (1988), 27(18): pp 6742–6751.

Seal, G., P. Arenaz and M.A. Sirover, *Purification and properties of the human placental uracil DNA glycosylase.* Biochim. Biophys. Acta., (1987), 925(2): pp 226–233.

Wittwer, C.U., G. Bauw, and H.E. Krokan, *Purification and determination of the NH2–terminal amino acid sequence of uracil–DNA glycosylase from human placenta.* Biochemistry, (1989), 28(2): pp 780–784.

Krokan, H. and C.U. Wittwer. *Uracil DNA–glycosylase from HeLa celles: general properties, substrate specificity and effect of uracil analogs*, Nucleic Acids Res., (1981), 9(11): pp 2599–2613.

Wittwer, C.U. and H. Krokan. *Uracil–DNA glycosylase in HeLa S3 cells: interconvertibility of 50 and 20 kDa forms and similarity of the nuclear and mitochondrial form of the enzyme*, Biochim. Biophys. Acta., (1985), 832(3): pp 308–318.

Myrnes, B. and C.U. Wittwer *Purification of the human O6–methylguanine–DNA methyltransferase and uracil–DNA glycosylase, the latter to apparent homogeneity*, Eur. J. Biochem., (1988), 173(2):pp 383–387.

Caradonna, S., et al. *Affinity purification and comparative analysis of two distinct human uracil–DNA glycosylases*, Exp. Cell Res., (1996), 222(2): pp 345–359.

Muller–Weeks, S., B. Mastran, and S. Caradonna. *The nuclear isoform of the highly conserved human uracil–DNA glycosylase is an Mr 36,000 phosphoprotein.* J. Biol. Chem., (1998), 273(34): pp 21909–21917.

Seal, G., R.J. Tallarida, and M.A. Sirover. *Purification and properties of the uracil DNA glycosylase from Bloom's syndrome.* Biochim. Biophys. Acta., (1991), 1097(4): pp 299–308.

Caradonna, S.J., and Y.C. Cheng. *Uracil DNA–glycosylase. Purification and properties of this enzyme isolated from blast cells of acute myelocytic leukemia patients.* J. Bio. Chem., (1980), 255(6): pp 2293–2300.

Talpaert–Borle, M., L. Clerici, and F. Campagnari. *Isolation and characterization of a uracil–DNA glycosylase from calf thymus.* J. Biol. Chem., (1979), 254(14): pp 6387–6391.

Talpaert–Borle, M., F. Campagnari, and D.M. Creissen. *Properties of purified uracil–DNA glycosylase from calf thymus. An in vitro study using synthetic DNA–like substrates.* J. Biol. Chem., (1982), 257(3): pp 1208–1214.

Guyer, R.B., J.M. Nonnemaker, and R.A. Deering. *Uracil–DNA glycosylase activity from Dictyostelium discoideum.* Biochim. Biophys. Acta., (1986), 868(4): pp 262–264.

Crosby, B., et al. *Purification and characterization of a uracil–DNA glycosylase from the yeast Saccharomyces cerevisiae.* Nucleic Acids Res., (1981), 9(21): pp 5797–5809.

Blaisell, P. and H. Warner. *Partial purification and characterization of a uracil–DNA glycosylase from wheat germ.* J. Biol. Chem., (1983), 258(3): pp 1603–1609.

Talpaert–Borle, M. and M. Liuzzi, *Base–excision repair in carrot cells. Partial purification and characterization of uracil–DNA glycosylase and apurinic/apyrimidinic endodeoxyribonuclease.* Eur. J. Biochem., (1982), 124(3): p 435–440.

Birch, D.J. and A.G. McLennan. *Uracil–DNA glycosylase in developing embyros of the brine shrimp (Artemia salina).* Biochem. Soc. Trans., (1980), 8(6): pp 730–731.

Lindahl, T., et al. *DNA N–glycosidases; properties of uracil–DNA glycosidase from Escherichia coli.* J. Biol. Chem., (1977), 252(10): pp 3286–3294.

Cone, R. et al. *Partial purification characterization of a uracil DNA N–glycosidase from Bacillus subtilis.* Biochemistry, (1977), 16(14): p 3194–3201.

Williams, M.V. and J.D. Pollack. *A mollicute (mycoplasma) DNA repair enzyme: purification and characterization of uracil–DNA glycosylase.* J. Bacteriol., (1990), 172(6): pp 2979–2985.

Kaboev, O.K., et al. *Uracil–DNA glycosylase from Bacillus stearothermophilus.* FEBS Lett., (1981), 132(2): pp 337–340.

Purnapatre, K. And U. Varshney. *Uracil DNA glycosylase from Mycobacterium smegmatis and its distinct biochemical properties.* Eur. J. Biochem., (1998), 256(3): pp 580–588.

Kaboev, O.K., L.A. Luchkina, and T.I. Kuziakina. *Uracil–DNA glycosylase of thermophilic Thermothrix thiopara.* J. Bacteriol., (1985), 164(1): pp 421–424.

Masters, C.I., B.E. Moseley, and K.W. Minton. *AP endonuclease and uracil DNA glycosylase activities in Deinococcus radiodurans.* Mutat Res., (1991), 254(3): pp 263–272.

Koulis, A., et al. *Uracil–DNA glycosylase activities in hyperthermophilic micro–organisms.* FEMS Microbiol. Letts., (1996), 143(2–3): pp 267–271.

Leblanc, J.P., et al. *Uracil–DNA glycosylase. Purification and properties of uracil–DNA glycosylase from Micrococcus luteus.* J. Biol. Chem., (1982), 257(7): pp 3477–3483.

Focher, F., et al. *Herpes simplex virus type 1 uracil–DNA glycosylase: isolation and selective inhibition by novel uracil derivatives.* Biochem. J., (1993), 292(Pt. 3): pp 883–889.

Winters, T.A. and M.V. Williams. *Purification and characterization of the herpes simplex virus type 2–encoded uracil–DNA glycosylase.* Virology, (1993), 195(2): pp 315–326.

Slupphaug, G., et al. *Nuclear and mitochondrial forms of human uracil–DNA glycosylase are encoded by the same gene.* Nucleic Acids Res., (1993), 21(11): pp 2579–2584.

Nilsen, H., et al. *Nuclear and mitochondrial uracil–DNA glycosylases are generated by alternative splicing and transcription from different positions in the UNG gene.* Nucleic Acids Res., (1997), 25(4): pp 750–755.

Bharati, S., et al. *Human mitochondrial uracil–DNA glycosylase preform (UNG1) is processed to two forms one of which is resistant to inhibition by AP sites.* Nucleic Acids Res., (1998), 26(21): pp 4953–4959.

Haug, T., et al., *Regulation of expression of nuclear and mitochondrial forms of human uracil–DNA glycosylase.* Nucleic Acids Res., (1998), 26(6): pp 1449–1457.

Otterlei, M., et al. *Nuclear and mitochondrial splice forms of human uracil–DNA glycosylase contain a complex nuclear localisation signal and a strong classical mitochondrial localisation signal, respectively.* Nucleic Acids Res., (1998), 26(20): pp 4611–4617.

Mol, C.D., et al. *Crystal structure and mutational analysis of human uracil–DNA glycosylase: Structural basis for specificity and catalysis*. Cell, (1995), 80(6): pp 869–878.

Savva, R., et al. *The structural basis of specific base–excision repair by uracil–DNA glycosylase*. Nature, (1995), 373(6514): pp 487–493.

Ravishankar, R., et al. *X–ray analysis of a complex of Escherichia coli uracil DNA glycosylase (EcUDG) with a proteinaceous inhibitor. The structure elucidation of a prokaryotic UDG*. Nucleic Acids Res., (1998), 26(21): pp 4880–4887.

Slupphaug, G., et al. *A nucleotide–flipping mechanism from the structure of human uracil–DNA glycosylase bound to DNA*. Nature, (1996), 384(6604): pp 87–92.

Parikh, S.S., et al. *Base excision repair initiation revealed by crystal structures and binding kinetics of human uracil–DNA glycosylase with DNA*. Embo. J., (1998), 17(17): pp 5214–5226.

Feller, G. and C. Gerday. *Psychrophilic enzymes: molecular basis of cold adaptation*. Cell Mol. Life Sci., (1997), 53(10): pp 830–841.

Kwok, S., and R. Higuchi. *Avoiding false positives with PCR*. Nature, (1989), 339: pp 237–238.

Longo, M.C., M.S. Berningr, and J.L. Hartley. *Use of uracil DNA glycosylase to control carry–over contamination in polymerase chain reactions*. Gene (1990), 93: pp 125–128.

Male, R., et al., *Molecular cloning and characterization of anionic and cationic variants of trypsin from Atlantic salmon*. Eur.J. Biochem., (1995), 232(2): pp 677–685.

Slupphaug, G., et al. *Properties of a recombinant human uracil–DNA glycosylase from the UNG gene and evidence that UNG encodes the major uracil–DNA glycosylase*. Biochemistry, (1995), 34(1): pp 128–138.

Bennett, S.E., M.I. Schimerlik, and D.W. Mosbaugh. *Kinetics of the uracil–DNA glycosylase/inhibitor protein association. Ung interaction with Ugi, nucleic acids, and uracil compounds*. J.Biol.Chem., (1993), 268(36): pp 26879–26885.

Karran, P., R, Cone, and E.C. Friedberg. *Specificity of the bacteriophage PBS2 induced inhibitor of uracil–DNA glycosylase*. Biochemistry, (1981), 20(21): pp 6092–6096.

Mol, C.D., et al. *Crystal structure of human uracil–DNA glycosylase in complex with a protein inhibitor: protein mimicry of DNA*. Cell, (1995), 82(5): pp 701–708.

von Hippel, P.H. and O.G. Berg. *Facilitated target location in biological systems*. J. Biol.Chem., (1989), 264(2): pp 675–678.

Dodson, M.L., M.L. Michaels, and R.S. Lloyd. *Unified catalytic mechanism for DNA glycosylases*. J. Biol. Chem., (1994), 269(52): pp 32709–32712.

Hamilton, R.W. and R.S. Lloyd. *Modulation of the DNA scanning activity of the Micrococcus luteus UV endonuclease*. J. Biol. Chem., (1989), 264(29): pp 17422–17427.

Berglund, G.I., et al. *Purification and characterization of pancreatic elastase from North Atlantic salmon (Salmo salari)*. Mol. Mar. Biol. Biotechnol., (1998), 7(2): pp 105–114.

Kunkel, T.A. *Rapid and efficient site–specific mutagenesis without phenotypic selection*. Proc. Natl. Acad. Sci., USA, (1985), 82: pp 488–492.

Varshney,U. and J.H. van de Sande. *Characterization of the ung1 mutation of Escherichia coli*. Nucleic Acids Res., (1989), 17(2): pp 813.

Amann, E., B. Ochs, and K.J. Abel. *Tightly regulated tac promoter vectors for the expression of unfused and fused proteins in Escherichia coli*. Gene, (1988), 69: pp 301–315.

English Title and Abstract of WO 97/20922 Dated Jun. 12, 1997.

Jaegr, S. et al. Molecular Cloning, Sequencing, and Expression of the Heat–Labile Uracil–DNA Glycosylase from a Marine Psychrophilic Bacterium, Strain BMTU 3346 Extremophilos (2000). No. 4PG 115–122.

Sobek, H. et al. Heat–Label Uracil–DNA Glycosylase: Purification and Characterization FEBS Letters (1996) No. 388 PG1–4.

Schmidt, M. et al."Application of Heat–Labile Uracil–DNA Glycosylace in Improved Carryover Prevention Technique." Biochemica, No. 2 (1996) pp 13–15.

Sobek, H. "Heat–Labile Uraccil–DNA Glycosylase from a Psychrophillc Marine Bacterium."Conference Papers Brothechno. Appl. Gold Adapted Organisms, vol. 75.

Mol, Clifford. et al."Crystal Structure and Mutational Analysis of Human Uracil–DNA Glycosylase: Structure Basis for Specific and Catalysis." Cell, vol. 80 (1995) pp 869–878.

Savva, R., et al. "Nucleotide mimicry in the crystal structure of the uracil–DNA glycosylase–uracil glycosylase inhibitor protein complex." Nature Structural Biology, vol. 2, No. 9 (1995) pp 752–757.

Outzen, H. et al. "Temperature and pH Sensitivity of Trypsins from Atlantic Salmon (*Salmo salar*) in Comparison with Bovine and Porcine Trypsin." Comp. Biochem. Physiol., vol. 1158, No. 1 (1996) pp 33–45.

* cited by examiner

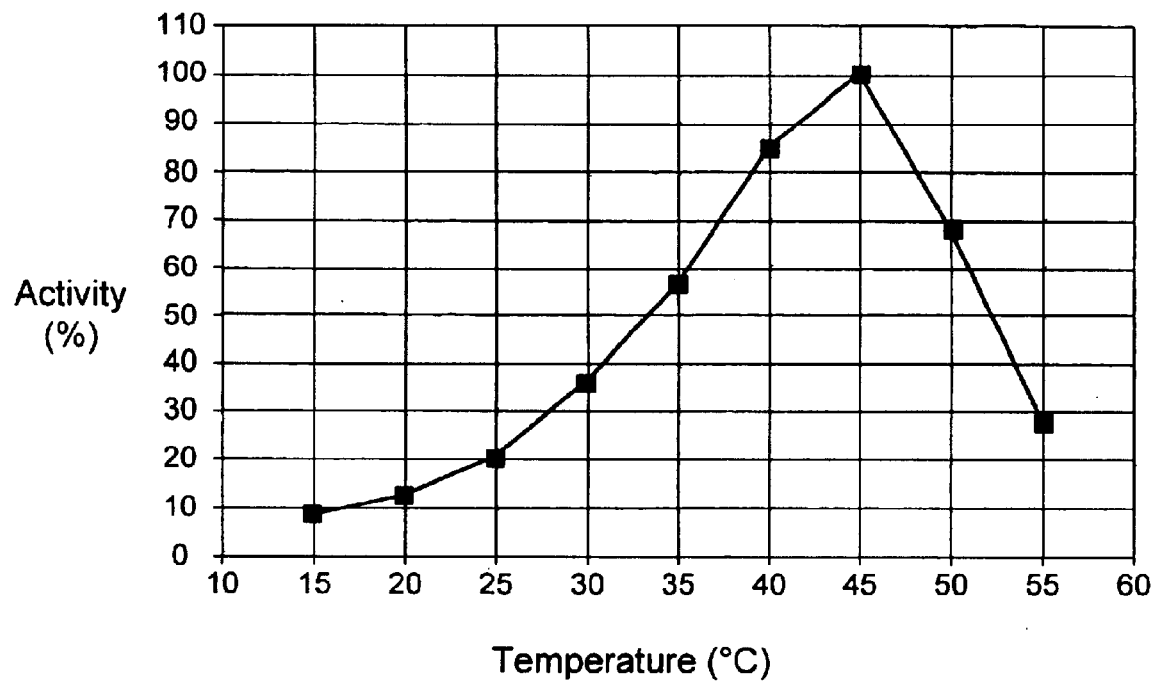
F I G. 5A
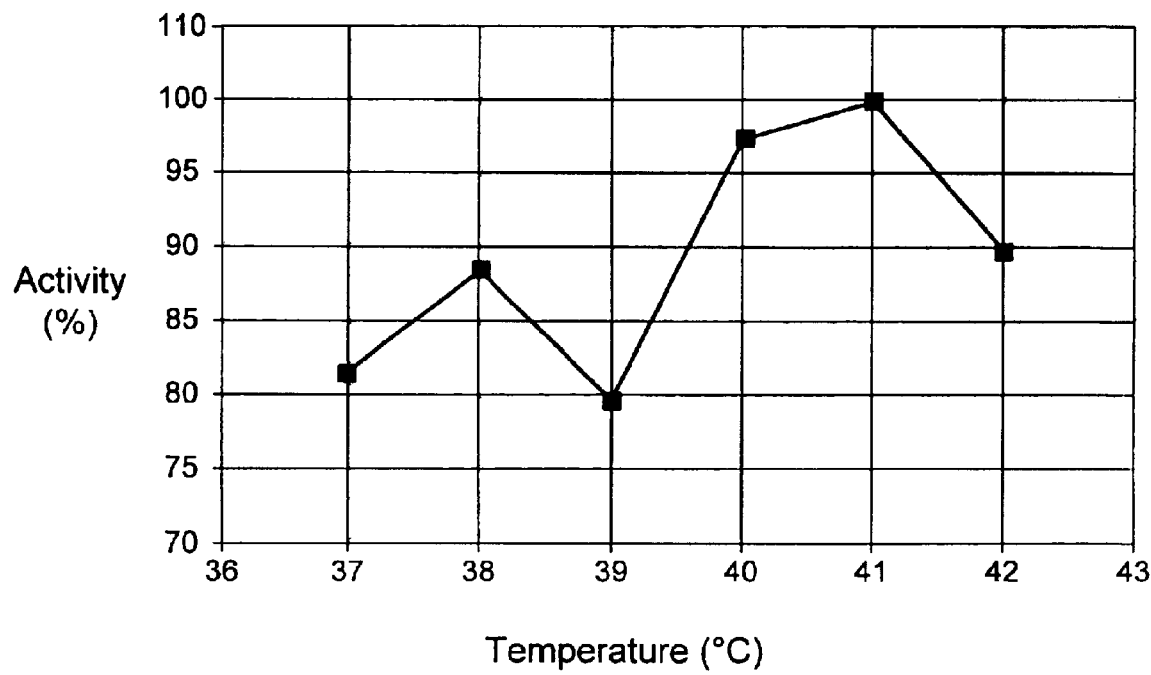
F I G. 5B (37°C)

SEQUENCE LISTING

<160> NUMBER OF SEQ ID NOS: 22

<210> SEQ ID NO 1
<211> LENGTH: 1283
<212> TYPE: DNA
<213> ORGANISM: GADUS MORHUA
<220> FEATURE:
<221> NAME/KEY: CDS
<222> LOCATION: (18)..(920)

<223> OTHER INFORMATION:

<400> SEQUENCE: 1

```
gacatccgct tgcaaat atg ttg ttc aag tta ggg tta tgc caa aga tgc         50
                   Met Leu Phe Lys Leu Gly Leu Cys Gln Arg Cys
                   1               5                   10 ata tca tca aat cgg gty tta cca ggt tta cta att ccc caa act tta        98
Ile Ser Ser Asn Arg Xaa Leu Pro Gly Leu Leu Ile Pro Gln Thr Leu
            15                  20                  25 tgt ttt tct aaa tta atg aag ata acg ccg aag aaa ctg agg tcc tca       146
Cys Phe Ser Lys Leu Met Lys Ile Thr Pro Lys Lys Leu Arg Ser Ser
        30                  35                  40 aat gtg gaa caa aag acg tca tcg cca cag ctt tca gtg gag cag ctg       194
Asn Val Glu Gln Lys Thr Ser Ser Pro Gln Leu Ser Val Glu Gln Leu
    45                  50                  55 gaa aga atg gcc aaa aat aag aaa gca gcg ctt gac aag att aga gca       242
Glu Arg Met Ala Lys Asn Lys Lys Ala Ala Leu Asp Lys Ile Arg Ala
60                  65                  70                  75 aaa gca acg cct gca ggt ttc gga gag act tgg aga aga gag ctg gct       290
Lys Ala Thr Pro Ala Gly Phe Gly Glu Thr Trp Arg Arg Glu Leu Ala
                80                  85                  90 gca gag ttt gaa aag cca tac ttc aaa caa ttg atg tcc ttt gta gct       338
Ala Glu Phe Glu Lys Pro Tyr Phe Lys Gln Leu Met Ser Phe Val Ala
            95                  100                 105 gat gag agg agc cgt cac acc gtc tac cca ccg gct gat caa gtg tac       386
Asp Glu Arg Ser Arg His Thr Val Tyr Pro Pro Ala Asp Gln Val Tyr
        110                 115                 120 agt tgg aca gag atg tgt gac att caa gat gtg aaa gta gtg att cta       434
Ser Trp Thr Glu Met Cys Asp Ile Gln Asp Val Lys Val Val Ile Leu
    125                 130                 135 ggc cag gac cct tac cac ggt ccc aac caa gca cat gga ctc tgt ttc       482
Gly Gln Asp Pro Tyr His Gly Pro Asn Gln Ala His Gly Leu Cys Phe
140                 145                 150                 155 agt gtg caa aag cca gtt ccc cct ccc ccc agt ctc gtg aac ata tac       530
Ser Val Gln Lys Pro Val Pro Pro Pro Pro Ser Leu Val Asn Ile Tyr
                160                 165                 170 aaa gaa ttg tgt acc gac att gat ggc ttc aag cat cct gga cat gga       578
Lys Glu Leu Cys Thr Asp Ile Asp Gly Phe Lys His Pro Gly His Gly
            175                 180                 185 gat cta agc gga tgg gca aaa caa ggg gtg ctg ctg ctt aac gcg gtg       626
Asp Leu Ser Gly Trp Ala Lys Gln Gly Val Leu Leu Leu Asn Ala Val
        190                 195                 200 ctg acc gtg cgg gcc cat cag gcc aac tcc cac aag gac aga ggc tgg       674
Leu Thr Val Arg Ala His Gln Ala Asn Ser His Lys Asp Arg Gly Trp
205                 210                 215 gag acc ttc acc gac gct gtg atc aag tgg ctg agc gtc aac cgg gaa       722
Glu Thr Phe Thr Asp Ala Val Ile Lys Trp Leu Ser Val Asn Arg Glu
220                 225                 230                 235 gga gtg gtt ttc ctg ttg tgg ggc tca tac gcc cat aag aag gga gcg       770
Gly Val Val Phe Leu Leu Trp Gly Ser Tyr Ala His Lys Lys Gly Ala
                240                 245                 250 acc atc gac agg aaa cgt cac cat gtc ttg caa gct gtt cat cca tct       818
Thr Ile Asp Arg Lys Arg His His Val Leu Gln Ala Val His Pro Ser
            255                 260                 265 cct ttg tct gct cat cgt ggg ttc ctt ggt tgt aag cac ttc tcc aag       866
Pro Leu Ser Ala His Arg Gly Phe Leu Gly Cys Lys His Phe Ser Lys
        270                 275                 280 gct aac ggg ctg ctg aaa cta tct ggg acg gag cct ata aac tgg aga       914
Ala Asn Gly Leu Leu Lys Leu Ser Gly Thr Glu Pro Ile Asn Trp Arg
285                 290                 295
```

```
gca ctc taactctttta tgctgcctta tactgttaac tgttttaaga tgaacatcac       970
Ala Leu
300 actatatttt ctacagcttt tccaagttca aaccaatcta taagctttca tttgtctttt      1030 ggaatgatgc tgcttttggt cggttttaga tacttaaaac actttaccac tctgccatgt     1090 tgactcatgt tcagtcaata taactttcac aacttgaaca aaaatgttat tttataattg     1150 attatattct gtacattaaa gattgttttt ttcccaggct gtttcatagg tactaggata     1210 ttaaactgtt attaacctat tttccatgat gtcaactgct taagttttta tgcagaaata     1270 aattatatat tta                                                        1283
```

<210> SEQ ID NO 2
<211> LENGTH: 301
<212> TYPE: PRT
<213> ORGANISM: GADUS MORHUA
<220> FEATURE:
<221> NAME/KEY: misc_feature
<222> LOCATION: (17)..(17)
<223> OTHER INFORMATION: The 'Xaa' at location 17 stands for Val.

<400> SEQUENCE: 2

```
Met Leu Phe Lys Leu Gly Leu Cys Gln Arg Cys Ile Ser Ser Asn Arg
1               5                   10                  15

Xaa Leu Pro Gly Leu Leu Ile Pro Gln Thr Leu Cys Phe Ser Lys Leu
                20                  25                  30

Met Lys Ile Thr Pro Lys Lys Leu Arg Ser Ser Asn Val Glu Gln Lys
            35                  40                  45

Thr Ser Ser Pro Gln Leu Ser Val Glu Gln Leu Glu Arg Met Ala Lys
        50                  55                  60

Asn Lys Lys Ala Ala Leu Asp Lys Ile Arg Ala Lys Ala Thr Pro Ala
65                  70                  75                  80

Gly Phe Gly Glu Thr Trp Arg Arg Glu Leu Ala Ala Glu Phe Glu Lys
                85                  90                  95

Pro Tyr Phe Lys Gln Leu Met Ser Phe Val Ala Asp Glu Arg Ser Arg
            100                 105                 110

His Thr Val Tyr Pro Pro Ala Asp Gln Val Tyr Ser Trp Thr Glu Met
        115                 120                 125

Cys Asp Ile Gln Asp Val Lys Val Val Ile Leu Gly Gln Asp Pro Tyr
130                 135                 140

His Gly Pro Asn Gln Ala His Gly Leu Cys Phe Ser Val Gln Lys Pro
145                 150                 155                 160

Val Pro Pro Pro Ser Leu Val Asn Ile Tyr Lys Glu Leu Cys Thr
                165                 170                 175

Asp Ile Asp Gly Phe Lys His Pro Gly His Gly Asp Leu Ser Gly Trp
            180                 185                 190

Ala Lys Gln Gly Val Leu Leu Asn Ala Val Leu Thr Val Arg Ala
        195                 200                 205

His Gln Ala Asn Ser His Lys Asp Arg Gly Trp Glu Thr Phe Thr Asp
    210                 215                 220

Ala Val Ile Lys Trp Leu Ser Val Asn Arg Glu Gly Val Val Phe Leu
225                 230                 235                 240

Leu Trp Gly Ser Tyr Ala His Lys Lys Gly Ala Thr Ile Asp Arg Lys
                245                 250                 255

Arg His His Val Leu Gln Ala Val His Pro Ser Pro Leu Ser Ala His
            260                 265                 270
```

```
Arg Gly Phe Leu Gly Cys Lys His Phe Ser Lys Ala Asn Gly Leu Leu
        275                 280                 285

Lys Leu Ser Gly Thr Glu Pro Ile Asn Trp Arg Ala Leu
        290                 295                 300

<210> SEQ ID NO 3
<211> LENGTH: 1355
<212> TYPE: DNA
<213> ORGANISM: GADUS MORHUA
<220> FEATURE:
<221> NAME/KEY: CDS
<222> LOCATION: (90)..(992)
<223> OTHER INFORMATION:

<400> SEQUENCE: 3
gatggtttag gaggatagta ctttgacact ggttagcgaa ggggaaaacg gagttattgt        60
gcatatcgtt ttagccctac gtttaaaaa atg att ggt caa cag cat atc aac       113
                                Met Ile Gly Gln Gln His Ile Asn
                                  1               5 tct ttc ttc tca cca gtt tca aaa aag aga gtt tca aag gaa tta ggt       161
Ser Phe Phe Ser Pro Val Ser Lys Lys Arg Val Ser Lys Glu Leu Gly
         10                  15                  20 aaa acc gaa aag cat gcc gaa gaa gtt cag ata acg ccg aag aaa ctg       209
Lys Thr Glu Lys His Ala Glu Glu Val Gln Ile Thr Pro Lys Lys Leu
 25                  30                  35                  40 agg tcc tca aat gtg gaa caa aag acg tca tcg cca cag ctt tca gtg       257
Arg Ser Ser Asn Val Glu Gln Lys Thr Ser Ser Pro Gln Leu Ser Val
                 45                  50                  55 gag cag ctg gaa aga atg gcc aaa aat aag aaa gca gcg ctt gac aag       305
Glu Gln Leu Glu Arg Met Ala Lys Asn Lys Lys Ala Ala Leu Asp Lys
             60                  65                  70 att aga gca aaa gca acg cct gca ggt ttc gga gag act tgg aga aga       353
Ile Arg Ala Lys Ala Thr Pro Ala Gly Phe Gly Glu Thr Trp Arg Arg
         75                  80                  85 gag ctg gct gca gag ttt gaa aag cca tac ttc aaa caa ttg atg tcc       401
Glu Leu Ala Ala Glu Phe Glu Lys Pro Tyr Phe Lys Gln Leu Met Ser
 90                  95                 100 ttt gta gct gat gag agg agc cgt cac acc gtc tac cca ccg gct gat       449
Phe Val Ala Asp Glu Arg Ser Arg His Thr Val Tyr Pro Pro Ala Asp
105                 110                 115                 120 caa gtg tac agt tgg aca gag atg tgt gac att caa gat gtg aaa gta       497
Gln Val Tyr Ser Trp Thr Glu Met Cys Asp Ile Gln Asp Val Lys Val
                125                 130                 135 gtg att cta ggc cag gac cct tac cac ggt ccc aac caa gca cat gga       545
Val Ile Leu Gly Gln Asp Pro Tyr His Gly Pro Asn Gln Ala His Gly
            140                 145                 150 ctc tgt ttc agt gtg caa aag cca gtt ccc cct ccc cca agt ctc gtg       593
Leu Cys Phe Ser Val Gln Lys Pro Val Pro Pro Pro Pro Ser Leu Val
        155                 160                 165 aac ata tac aaa gaa ttg tgt acc gac att gat ggc ttc aag cat cct       641
Asn Ile Tyr Lys Glu Leu Cys Thr Asp Ile Asp Gly Phe Lys His Pro
    170                 175                 180 gga cat gga gat cta agc gga tgg gca aaa caa ggg gtg ctg ctg ctt       689
Gly His Gly Asp Leu Ser Gly Trp Ala Lys Gln Gly Val Leu Leu Leu
185                 190                 195                 200 aac gcg gtg ctg acc gtg cgg gcc cat cag gcc aac tcc cac aag gac       737
Asn Ala Val Leu Thr Val Arg Ala His Gln Ala Asn Ser His Lys Asp
                205                 210                 215 aga ggc tgg gag acc ttc acc gac gct gtg atc aag tgg ctg agc gtc       785
Arg Gly Trp Glu Thr Phe Thr Asp Ala Val Ile Lys Trp Leu Ser Val
```

-continued

```
                    220                 225                 230
aac cgg gaa gga gtg gtt ttc ctg ttg tgg ggc tca tac gcc cat aag         833
Asn Arg Glu Gly Val Val Phe Leu Leu Trp Gly Ser Tyr Ala His Lys
            235                 240                 245 aag gga gcg acc atc gac agg aaa cgt cac cat gtc ttg caa gct gtt         881
Lys Gly Ala Thr Ile Asp Arg Lys Arg His His Val Leu Gln Ala Val
    250                 255                 260 cat cca tct cct ttg tct gct cat cgt ggg ttc ctt ggt tgt aag cac         929
His Pro Ser Pro Leu Ser Ala His Arg Gly Phe Leu Gly Cys Lys His
265                 270                 275                 280 ttc tcc aag gct aac ggg ctg ctg aaa cta tct ggg acg gag cct ata         977
Phe Ser Lys Ala Asn Gly Leu Leu Lys Leu Ser Gly Thr Glu Pro Ile
                285                 290                 295 aac tgg aga gca ctc taactcttta tgctgcctta tactgttaac tgttttaaga        1032
Asn Trp Arg Ala Leu
                300 tgaacatcac actatatttt ctacagcttt tccaagttca aaccaatcta taagctttca      1092 tttgtctttt ggaatgatgc tgcttttggt cggttttaga tacttaaaac actttaccac      1152 tctgccatgt tgactcatgt tcagtcaata taactttcac aacttgaaca aaaatgttat      1212 tttataattg attatattct gtacattaaa gattgttttt ttcccaggct gtttcatagg      1272 tactaggata ttaaactgtt attaacctat tttccatgat gtcaactgct taagttttta      1332 tgcagaaata aattatatat tta                                              1355

<210> SEQ ID NO 4
<211> LENGTH: 301
<212> TYPE: PRT
<213> ORGANISM: GADUS MORHUA

<400> SEQUENCE: 4

Met Ile Gly Gln Gln His Ile Asn Ser Phe Phe Ser Pro Val Ser Lys
1               5                   10                  15

Lys Arg Val Ser Lys Glu Leu Gly Lys Thr Glu Lys His Ala Glu Glu
            20                  25                  30

Val Gln Ile Thr Pro Lys Lys Leu Arg Ser Ser Asn Val Glu Gln Lys
        35                  40                  45

Thr Ser Ser Pro Gln Leu Ser Val Glu Gln Leu Glu Arg Met Ala Lys
    50                  55                  60

Asn Lys Lys Ala Ala Leu Asp Lys Ile Arg Ala Lys Ala Thr Pro Ala
65                  70                  75                  80

Gly Phe Gly Glu Thr Trp Arg Arg Glu Leu Ala Ala Glu Phe Glu Lys
                85                  90                  95

Pro Tyr Phe Lys Gln Leu Met Ser Phe Val Ala Asp Glu Arg Ser Arg
            100                 105                 110

His Thr Val Tyr Pro Pro Ala Asp Gln Val Tyr Ser Trp Thr Glu Met
        115                 120                 125

Cys Asp Ile Gln Asp Val Lys Val Val Ile Leu Gly Gln Asp Pro Tyr
    130                 135                 140

His Gly Pro Asn Gln Ala His Gly Leu Cys Phe Ser Val Gln Lys Pro
145                 150                 155                 160

Val Pro Pro Pro Ser Leu Val Asn Ile Tyr Lys Glu Leu Cys Thr
                165                 170                 175

Asp Ile Asp Gly Phe Lys His Pro Gly His Gly Asp Leu Ser Gly Trp
            180                 185                 190

Ala Lys Gln Gly Val Leu Leu Leu Asn Ala Val Leu Thr Val Arg Ala
```

-continued

```
                195                 200                 205
His Gln Ala Asn Ser His Lys Asp Arg Gly Trp Glu Thr Phe Thr Asp
    210                 215                 220

Ala Val Ile Lys Trp Leu Ser Val Asn Arg Glu Gly Val Val Phe Leu
225                 230                 235                 240

Leu Trp Gly Ser Tyr Ala His Lys Lys Gly Ala Thr Ile Asp Arg Lys
                245                 250                 255

Arg His His Val Leu Gln Ala Val His Pro Ser Pro Leu Ser Ala His
        260                 265                 270

Arg Gly Phe Leu Gly Cys Lys His Phe Ser Lys Ala Asn Gly Leu Leu
    275                 280                 285

Lys Leu Ser Gly Thr Glu Pro Ile Asn Trp Arg Ala Leu
    290                 295                 300

<210> SEQ ID NO 5
<211> LENGTH: 30
<212> TYPE: PRT
<213> ORGANISM: GADUS MORHUA

<400> SEQUENCE: 5

Glu Gly Ser Asp His Arg Gln Glu Thr Ser Pro Cys Leu Ala Ser Ser
1               5                   10                  15

Ser Ser Ile Ser Phe Val Cys Ser Ser Trp Val Pro Trp Leu
            20                  25                  30

<210> SEQ ID NO 6
<211> LENGTH: 5
<212> TYPE: PRT
<213> ORGANISM: GADUS MORHUA

<400> SEQUENCE: 6

Ala Leu Leu Gln Gly
1               5

<210> SEQ ID NO 7
<211> LENGTH: 16
<212> TYPE: PRT
<213> ORGANISM: GADUS MORHUA

<400> SEQUENCE: 7

Arg Ala Ala Glu Thr Ile Trp Asp Gly Ala Tyr Lys Leu Glu Ser Thr
1               5                   10                  15

<210> SEQ ID NO 8
<211> LENGTH: 27
<212> TYPE: DNA
<213> ORGANISM: ARTIFICIAL SEQUENCE
<220> FEATURE:
<223> OTHER INFORMATION: Artificial Sequence - Primer used to generate
      cDNA of a fragment of UNG gene

<400> SEQUENCE: 8
tacggctgcg agaagacgac agaaggg                                        27

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: Artificial Sequence - Primer used to prepare
      cDNA of a fragment of UNG gene

<400> SEQUENCE: 9
```
tacggctccg agaagacgac agaa 24

<210> SEQ ID NO 10
<211> LENGTH: 17
<212> TYPE: DNA
<213> ORGANISM: ARTIFICIAL SEQUENCE
<220> FEATURE:
<223> OTHER INFORMATION: Artificial Sequence - Primer used to generate
      cDNA portion of cUNG gene

<400> SEQUENCE: 10
gghcargayc cctayca 17

<210> SEQ ID NO 11
<211> LENGTH: 18
<212> TYPE: DNA
<213> ORGANISM: ARTIFICIAL SEQUENCE
<220> FEATURE:
<223> OTHER INFORMATION: Artificial Sequence - Primer used to generate
      cDNA of a fragment of gene

<400> SEQUENCE: 11
dccccasags agraavac 18

<210> SEQ ID NO 12
<211> LENGTH: 27
<212> TYPE: DNA
<213> ORGANISM: ARTIFICIAL SEQUENCE
<220> FEATURE:
<223> OTHER INFORMATION: Artificial Sequence - Primer used to generate
      fragment of UNG gene

<400> SEQUENCE: 12
tgtaccgaca ttgatggctt caagcat 27

<210> SEQ ID NO 13
<211> LENGTH: 27
<212> TYPE: DNA
<213> ORGANISM: ARTIFICIAL SEQUENCE
<220> FEATURE:
<223> OTHER INFORMATION: Artificial Sequence - Primer used to generate
      fragment of UNG gene

<400> SEQUENCE: 13
cccatccgct tagatctcca tgtccag 27

<210> SEQ ID NO 14
<211> LENGTH: 28
<212> TYPE: DNA
<213> ORGANISM: Artificial
<220> FEATURE:
<223> OTHER INFORMATION: Artificial Sequence - Primer used to generate
      fragment of UNG gene

<400> SEQUENCE: 14
ccatcctaat tacgactcac tatagggc 28

<210> SEQ ID NO 15
<211> LENGTH: 30
<212> TYPE: DNA
<213> ORGANISM: ARTIFICIAL SEQUENCE
<220> FEATURE:
<223> OTHER INFORMATION: Artificial Sequence - Primer used to generate
      fragment of RACE fragment of UNG gene

<400> SEQUENCE: 15
atggaattcg attgagattg gcgcctttgg 30

<210> SEQ ID NO 16
<211> LENGTH: 30
<212> TYPE: DNA
<213> ORGANISM: ARTIFICIAL SEQUENCE
<220> FEATURE:
<223> OTHER INFORMATION: Artificial Sequence - Primer used to construct
      rcUNG delta 74 gene

<400> SEQUENCE: 16
accatggaat cccaaaagc aacgcctgca                                           30

<210> SEQ ID NO 17
<211> LENGTH: 37
<212> TYPE: DNA
<213> ORGANISM: ARTIFICIAL SEQUENCE
<220> FEATURE:
<223> OTHER INFORMATION: Artificial Sequence - Primer used to construct
      rcUNG delta 74 gene

<400> SEQUENCE: 17
gagctcgtcg acttagagtg cctctccagt ttatagg                                  37

<210> SEQ ID NO 18
<211> LENGTH: 33
<212> TYPE: DNA
<213> ORGANISM: ARTIFICIAL SEQUENCE
<220> FEATURE:
<223> OTHER INFORMATION: Artificial Sequence - Primer used to construct
      rcUNG delta 81 gene

<400> SEQUENCE: 18
accatggaat tcttcggaga gacttggaga aga                                      33

<210> SEQ ID NO 19
<211> LENGTH: 54
<212> TYPE: DNA
<213> ORGANISM: ARTIFICIAL SEQUENCE
<220> FEATURE:
<223> OTHER INFORMATION: Artificial Sequence - Primer used to construct
      rcUNG delta 74 gene

<400> SEQUENCE: 19
atggaattcg caaagcaac gcctgcaggt ttcggagaga cttggcgtcg tcag                 54

<210> SEQ ID NO 20
<211> LENGTH: 42
<212> TYPE: DNA
<213> ORGANISM: ARTIFICIAL SEQUENCE
<220> FEATURE:
<223> OTHER INFORMATION: Artificial Sequence - Primer used to construct
      rcUNG delta 81 gene

<400> SEQUENCE: 20
atggaattct tcggagagac ttggcgtcgt tgagctggct gc                             42

<210> SEQ ID NO 21
<211> LENGTH: 47
<212> TYPE: DNA
<213> ORGANISM: ARTIFICIAL
<220> FEATURE:
<223> OTHER INFORMATION: Artificial Sequence - Primer used to prepare
      rcUNG gene

<400> SEQUENCE: 21
tctctcgaga aaagagaggc tgaagctccc attgacgatg aggatga                        47

```
<210> SEQ ID NO 22
<211> LENGTH: 35
<212> TYPE: DNA
<213> ORGANISM: ARTIFICIAL
<220> FEATURE:
<223> OTHER INFORMATION: Artificial Sequence - Primer used to prepare
      rcUNG gene

<400> SEQUENCE: 22
gtagaattcg gatccatgtc tcctccagtc tagat                              35
```

COD URACIL-DNA GLYCOSYLASE, GENE CODING THEREFORE, RECOMBINANT DNA CONTAINING SAID GENE OR OPERATIVE PARTS THEREOF, A METHOD FOR PREPARING SAID PROTEIN AND THE USE OF SAID PROTEIN OR SAID OPERATIVE PARTS THEREOF IN MONITORING OR CONTROLLING PCR

FIELD OF INVENTION

The present invention relates to a novel enzyme present in cod liver, a DNA sequence encoding the enzyme or operative—or biologically active parts thereof, a novel recombinant DNA comprising the gene or the operative parts thereof, a method of preparing the enzyme from cod liver and from bacteria carrying the gene, the bacteria carrying the gene per se, and the use of the protein in monitoring and/or controlling PCR or related reaction systems.

DESCRIPTION OF PRIOR ART

Uracil in DNA may result from the incorporation of dUTP instead of dTTP during replication or from deamination of cytosine in DNA. The latter results in a mutation at the next round of replication. The enzyme Uracil-DNA glycosylase (UDG, EC 3.2.2.3) functions as a repair enzyme for such damage to DNA in that the uracil base is excised from the DNA backbone (Lindahl 1994), creating an apyrimidinic site which is recognised by other DNA repair enzymes. This enzyme is crucial to maintain DNA integrity, and has therefore been found in a variety of organisms; virus, prokaryotes and eukaryotes.

Uracil-DNA glycosylase (UNG or UDG) catalyses the hydrolysis of the N-glycosylic bond between the deoxyribose sugar and the base in uracil-containing DNA, and was first isolated and characterized from *Escherichia coli* (1). This is the first step in the base excision repair (BER) pathway of removing uracil from DNA (2), and the apyrimidinic site generated is thereafter repaired by an AP endonuclease, phosphodiesterase, DNA polymerase and DNA ligase (other enzymes) in the BER pathway (3–5).

Several classes of uracil-DNA glycosylases (UDG) have been described. The major cellular form of UNG is UNG encoded by the UNG-gene (6). Other classes comprises the cyclin-like human UDG2 (7,8), single-strand selective monofunctional UDG SMUG1 from human and *Xenopus* (9), G/T:U specific mismatch DNA glycosylase (MUG) isolated from *E. coli* (10,11) and *Thermotoga maritima* UDG (TMUDG) (12).

UNG is a monomeric protein, about 25–35 kD in size. It is not dependent of any cofactors or divalent cations and is highly conserved among different species (13). UNG is, however, affected by ionic strength. The UNG enzyme has been shown to act in a processive "sliding mechanism", where it locates sequential uracil-residues prior to dissociation from DNA (14,15), and a distributive "random hit" mechanism (16). UNG has previously been isolated and characterised from rat liver (17–19), human cells and tissues (20–28), calf thymus (29,30), slime mold (31), yeast (32), plants (33,34), brine shrimp (35), procaryotes (1,36–45) and viruses (46,47).

In human and rat both a mitochondria and nuclear UNG have been isolated (18,25). In human (and mouse) cells these two are encoded by the same gene (UNG) (48,49). By two different transcription start sites and alternative splicing, two forms are generated which differ only in the N-terminal signal sequence, which targets the enzyme to the nucleus (UNG-2) and mitochondria (UNG1), respectively (49). Recently, several studies have been done to further study the N-terminal signal sequence and targeting of UNG to the nucleus and mitochondria (50–52), revealing the nuclear UNG2 to be phosphorylated (26). The crystal structures of UNG from human, herpes simplex virus and *E. coli* have been solved (53–55). The active site residues are conserved and the mode of action in these enzymes seems to be the same with a nucleotide flipping mechanism to remove uracil from DNA (56,57).

Enzymes from cold adapted organisms, such as the Atlantic cod (*Gadus morhua*), have to compensate for the reduction of chemical reaction rates at low temperatures in order to maintain sufficient metabolic activities. This can be achieved by higher transcriptional/translational levels or improved catalytic efficiency ($k_{cat}/K_M$). Higher catalytic efficiencies can be reached by a more flexible structure, compared to their mesophile counterparts, which provides enhanced ability to undergo conformational changes during catalysis. The reduced stability to pH, temperature and denaturing agents is regarded as a consequence of the conformational flexibility (58).

The present invention concerns the purification and characterization of a heat-labile uracil-DNA glycosylase from a cold-adapted organism, and which has utility as an enzyme efficient in carry-over prevention in DNA-copying reactions (PCR, LCR etc.). The enzyme isolated according to the present invention has similar characteristics as previously described UNGs with respect to molecular weight, isoelectric point, pH and NaCl-optimum. However, the enzyme according to the present invention has been shown to be more pH-labile and heat-labile and has a higher relative activity at low temperatures, compared to a recombinant mesophilic human UNG, making it a better candidate in carry-over prevention tests as indicated supra.

UNG (or UDG) from *Escherichia coli* has been commercially available for use in carry-over prevention when amplifying DNA material.

Various techniques may be employed to amplify specific DNA sequences on basis of a DNA template. Common techniques are the polymerase chain reaction (PCR) system (U.S. Pat. Nos. 4,683,195; 4,683,202; and 4,965,188), the ligase amplification system (PCT patent publication No. 89/09835), the self-sustained sequence replication system (EP No. 329,822 and PCT patent publication No. 90/06995), the transcription-based amplification system (PCT patent publication No. 89/01050 and EP No. 310,229) and the Qβ RNA replicase system (U.S. Pat. No. 4,957,858). These techniques are very sensitive in that they may produce detectable DNA amounts from very few copies of a target DNA sequence. Accordingly the techniques are very sensitive to contamination by DNA from the environment. The major source of contamination is products from previously performed up-scaling reactions, e.g. PCR reactions (59).

To overcome this problem a method to discriminate between target DNA and contaminating DNA from prior reactions, e.g. PCR product DNA, has been developed (60). In essence, all amplification reactions are carried out using dUTP to replace dTTP thus incorporating uracil into DNA in place of thymidine. All subsequent reaction mixtures are then treated with UDG (or UNG). A following heat treatment degrades the contaminating DNA by hydrolysis of the phospho diester bond at abasic sites. Also, the heat treatment is supposed to inactivate the UDG enzyme.

However, the UDG (or UNG) enzyme from *E. coli* is not completely inactivated by heat treatment, and the inactivation is not completely irreversible (60). This affects the upscaling reaction, e.g. PCR reaction, product integrity, since the products are degraded by residual UDG enzyme activity. In order to avoid this, the subsequent addition of enzyme inhibitor to UDG has been used (U.S. Pat. No. 5,536,649).

It would however, be preferable to avoid using the subsequent inhibitor because this represents an extra step in the reaction procedure, residual contamination by the inhibitor may be present in subsequent reactions, and the purchase of inhibitor represents an extra cost when performing a PCR reaction as disclosed supra.

Thus it would be preferable to use an UNG (or UDG) enzyme which is certain to be destroyed/inactivated by the heat treatment following the PCR reaction, thus avoiding the addition of specific chemical inhibitors for the UDG enzyme.

BRIEF DESCRIPTION OF THE FIGURES

FIG. 5 shows temperature optimum of cUNG. Due to prolonged incubation of the enzyme sample on ice during the experiment, activity is corrected with respect to the stability of the enzyme, as described in material and methods.

OBJECTS OF THE INVENTION

Figure 1:
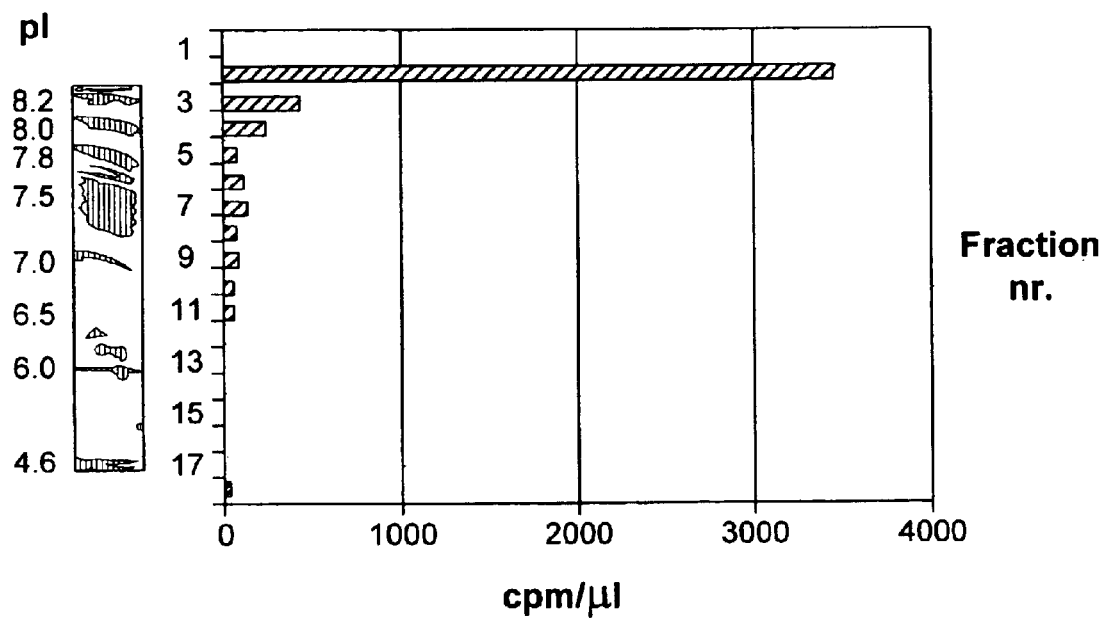
FIG. 1 shows pI determination of Atlantic cod UNG (cUNG). Following the isoelectric focusing using Phast Gel IEF 3–9, the gel was cut in pieces of 2 mm. Each piece was transferred to an eppendorf tube and incubated overnight at 4° C. Activity was then measured as described in material and methods.

It is an object of the present invention to provide a novel UNG (or UDG) enzyme which is functional in carry-over prevention techniques for DNA amplification reactions, e.g. PCR, indicated supra, and which is completely and irreversibly inactivated by the heat treatment normally performed in PCR reaction cycles.

Furthermore it is an object of the present invention to provide a DNA sequence coding for such an enzyme or an active part thereof, a vector or vector system (e.g. a virus, a plasmid, a cosmid, etc.) carrying such a DNA sequence and a micro organism including such a vector.

It is also an object of the present invention to provide a method for efficient production of the enzyme or an active part thereof by using genetic engineering techniques.

DETAILED DESCRIPTION OF THE INVENTION

Enzymes from cold adapted organisms living in cold habitats, such as the Atlantic cod (*Gadus morhua*), have to compensate the reduction of chemical reaction rates at low temperatures to maintain sufficient metabolic activities. This can be done by a higher transcription/translational level, or improved catalytic efficiency ($k_{cat}/K_M$). This higher efficiency is reached with a more flexible structure, compared to their mesophile counterparts, which provides enhanced ability to undergo conformational changes during catalysis. The reduced stability to pH, temperature and denaturing agents is regarded as a consequence of the conformational flexibility (58).

In view of the disadvantages with contaminations of UDG according to prior art in carry-over prevention procedures when amplifying DNA sequences (PCR, LCR) it would be very convenient to provide a UDG (or UNG) enzyme which was 100% degraded by simple heat treatment. It has now been found that a UNG (or UDG) enzyme isolated from cod has this valuable property. The cod-UNG enzyme isolated according to the present invention has a similar molecular weight, isoelectric point pH- and NaCl-optimum as previously described UNGs, but the present cod UNG is more pH- and heat-labile and has a higher relative activity at low temperatures as compared to a recombinant mesophilic human UNG.

The enzyme according to the present invention has uracil-DNA glycosylase activity and is completely inactivated when heated above about 60° C. It must be understood that this temperature treshold may vary within a range of a few degrees.

Preferably the enzyme according to the invention has an amino acid sequence as shown in SEQ ID NOs: 2 or 4, or a biologically functional part thereof.

The enzyme according to the present invention is preferably derived from an organism adapted to a cold environment, more preferably the organism is eukaryotic, and most preferably the organism is Atlantic cod.

A DNA-sequence encoding for the novel enzyme as defined in the patent claims is another aspect of the present invention. Preferably the DNA-sequence has a nucleotide sequence as given in the SEQ ID NOs. 2 or 4.

The DNA sequence according to the present invention is preferably including a promoter and contained in an expression vector such as a plasmid, a cosmid or a virus.

Further aspects of the invention is a micro organism comprising the said DNA-sequence of the invention as set out in the claims and use of the enzyme in monitoring and/or controlling a reaction system multiplying DNA-sequences such as PCR or LCR. In particular the enzyme of the invention is used in a carry-over prevention procedure.

Infra is disclosed an isolation procedure for the relevant cod UNG protein according to the invention, as well as isolation of DNA coding for this protein also its use in micro organisms for producing recombinantly the relevant UNG enzyme according to the invention, is disclosed.

EXAMPLE 1

Extraction, Purification and Characterization of codUNG (cUNG)

Purification of cUNG

Preparation of crude extract and all purification steps were performed at 4° C. The following materials were used; Q-sepharose FF, S-sepharose FF, Heparin sepharose HP (Hi-trap 5 ml), Poly-U-sepharose 4B, Superdex 75 HR10/30, Phast system and Phast IEF gels (3–9) and LMW gel filtration calibration kit were obtained from Amersham Pharmacia Biotech (Uppsala, Sweden). Deoxy[5$^3$-H]uridine 5'-triphosphate (19.3 Ci/mmol) was purchased from Amersham (U.K). Uracil-DNA glycosylase inhibitor (Ugi) was obtained from New England Biolabs (Beverly, Mass.), enzymes were purchased from Promega (Madison, Wis.). Protease inhibitors, calf-thymus DNA (D-1501), uracil, deoxyuridine and deoxyuridine-monophosphate were purchased from Sigma (St Lois, Mo.). All other reagents and buffers were purchased from Sigma and Merck (Darmstadt, Germany).

Preparation of Crude Extract

To 600 ml extract buffer (25 mM Tris/HCl 100 mM NaCl, 1 mM FDTA, 1 mM DTT, 10% glycerol, pH 8.0 (25° C.) 200 g of fresh cod liver was added and homogenized in an Atomix homogenizer (MSE, England). Before homogenization, the following protease inhibitor mix was added to the extract buffer: 1 mM PMSF, 1 µM pepstatine, 1 µM leupeptine, 10 µM TPCK and 10 µM TLCK (final concentrations). The homogenate was centrifuged at 28,000 g for 15 min and the supernatant was filtered through glasswool. Finally glycerol was added to 30%(v/v), and the cod liver crude extract was frozen at −70° C.

Q-sepharose Fast Flow 1 liter crude extract was diluted with 1 liter buffer A (25 mM Tris/HCl, 10 mM NaCl, 1 mM EDTA, 1% glycerol, pH 8.0) (Fraction 1). The sample was applied in two portions (1 liter each) on a Q-sepharose FF column (5.0/15), equilibrated with buffer A, and then washed with 250 ml buffer A, using a flow-rate of 10 ml/min. Proteins bound to the column were eluted with 200 ml buffer A+1.0 M NaCl, and the column was re-equilibrated with buffer A before the next part of the sample was applied, as mentioned above. The UNG-containing flowthrough and wash fractions from both two runs were pooled (Fraction 2, 2340 ml).

S-sepharose Fast Flow

Fraction 2 was applied to a S-Sepharose FF column (1.6/10) equilibrated in buffer A, flow rate 10 ml/min. The column was washed with 300 ml buffer A+60 mM NaCl, and eluted using a 200 ml linear gradient of 0.06–0.4 M NaCl in buffer A, flow-rate 5 ml/min. UNG-containing fractions were pooled (55 ml) and dialyzed overnight in buffer A (Fraction 3).

Heparine Sepharose High Performance

Fraction 3 was applied to a heparine sepharose HP Hi-Trap column (1.6/2.5) equilibrated in buffer A. The column was washed with 50 ml buffer A+60 mM NaCl and was eluted in a 50 ml linear gradient of 0.06–0.4 M NaCl in buffer A, flow-rate 1 ml/min. UNG-containing fractions were pooled (Fraction 4, 20 ml).

Poly-U Sepharose (4B)

Fraction 4 was then diluted 5 times in buffer A, and applied to a poly-U sepharose column (1.6/10) equilibrated in buffer A. The column was washed with 60 ml buffer A+60 mM NaCl and was eluted in a 200 ml linear gradient of 0.06–0.4 M NaCl in buffer A, flow-rate 1 ml/min. UNG-containing fractions were pooled (fraction 5, 70 ml).

Superdex75

Fraction 5 was concentrated to 200 µl using Ultrafree 15 and Ultrafree-MC ultracentrifugation filters (Millipore), cut-off 5K, and applied on the gel filtration column (HR 1.0/30) equilibrated in buffer A, with a flow-rate of 0.5 ml/min: Fractions (350 µl) were collected, and those containing UNG activity were pooled (fraction 6, 3 ml).

Preparation of Substrate by Nick-translation $^3$H-dUMP DNA was prepared by nick-translation and polymerase chain reaction (PCR). The nick-translated substrate was made in a total volume of 1 ml and contained 50 mM Tris/HCl, pH 7.2, 10 mM MgSO$_4$, 1 mM DTT, 250 µg calf thymus DNA purified by phenol/cloroform extraction and ethanol precipitated prior to use), 0.1 mM dATP, dCTP, dGTP and dUTP, where 3 µM of the dUTP was [$^3$H]-dUTP (19.3 Ci/mmol). Then 0.1 ng (5.35×10$^{-1}$ U) DNase I (bovine pancreas, Promega) was added and 30 seconds later 25 U of E. coli DNA polymerase, and the nick-translation mix was incubated at 21° C. for 24 hours. The nick-translated DNA was purified by phenol/chloroform extraction, and ethanol precipitation. DNA was resuspended in 50 µl TE-buffer and purified with a NAP-5 column (AP Biotech) equilibrated in TE-buffer (10 mM Tris/HCl, 1 mM EDTA, pH 8.0) to remove unincorporated nucleotides. Specific activity of the nick-substrate was 1.8×10$^5$ dpm/µg (425 cpm/pmol).

Preparation of Substrate by PCR

The PCR-produced substrate was used for all characterization experiments and consisted of a 761 bp fragment generated from cationic trypsinogen (sstrpIV) from Atlantic salmon (Salmo salar) (61). The PCR was carried out in a volume of 50 µl in a Perkin Elmer Cetus thermocycler. The PCR-mix contained 10 mM Tris/HCl, pH 8.3, 50 mM KCl, 6 mM MgCl$_2$, 0.37 mM dATP, dCTP, dGTP and dUTP, where 10.4 µM of dUTP was [$^3$H]-dUTP (17.0 Ci/mmol, Amersham), 700 pg template DNA (sstrpIV in a pgem7zt-vector), 2.5 µM of upstream and downstream primers and 2 U Taq polymerase (Roche, Switzerland). The PCR-reaction was done by 30 cycles of 94° C. for 1 min, 45° C. for 1 min and 72° C. for 1 min. Then an additional 2 U of Taq-polymerase was added and the PCR-reaction continued with 30 new cycles as described. The PCR-substrate was purified with QIAquick PCR-purification kit (Qiagen) as described by manufacturer, and eluted in 50×diluted TE-buffer, pH 8.0. Specific activity of the PCR-substrate was $5.9 \times 10^5$ dpm/µg (451 cpm/pmol). All characterization experiments were done using the PCR-substrate.

Detection of Uracil-DNA Glycosylase Activity (Standard Assay)

Uracil-DNA glycosylase activity was measured in a final volume of 20 µl, containing 70 mM Tris/HCl, 10 mM NaCl, 1 mM EDTA, 100 µg/ml BSA and 230 ng nick-substrate or 71 ng PCR-substrate. The reaction mixture was incubated 10 min at 37° C., and terminated with the addition of 20 µl of ice cold single stranded calf thymus DNA (1 mg/ml) and 500 µl 10% (w/v) TCA. Samples were incubated on ice for 15 min, and centrifuged at 16,000 g for 10 min. Supernatants with acid soluble $^3$H-uracil were analyzed using a liquid scintillation counter.

One unit of activity is defined as the amount of enzyme required to release 1 nmol of acid soluble uracil per minute at 37° C.

Analysis of Assay Products with Thin Layer Chromatography

Reaction products after assays were mixed with 20 nmol uracil, deoxyuridine and deoxyuridine monophosphate. Thin layer chromatography was preformed according to the method by Wang and Wang, using polyamide layer plates (BDH), and tetrachloromethane, acetic acid and acetone (4:1:4, by volume) as solvent (62). Spots detected under UV-light were cut out of the plate and radioactivity measured in a liquid scintillation counter.

Molecular-weight Determination

The molecular weight was determined by gel-filtration, and was performed with a Superdex 75 column (1.0/30) equilibrated in a buffer containing 25 mM Tris/HCl, 1.0 M NaCl, 1 mM EDTA, 1% glycerol, pH 8.0. The flow-rate was 0.5 ml/min, and activity was measured in the fractions collected (250 µl). Bovine serum albumin (BSA 67 kD), ovalbumin (43 kD), chymotrypsinogenA (25 kD) and ribonucleaseA (13.7 kD) were used as standards. Blue dextran and sodium chloride were used to determine void- ($V_0$) and intrinsic volume ($V_1$), respectively.

Protein Determination

Protein concentrations were determined with Coomassie® Protein Assay Reagent G-250 (Pierce, New York, N.Y.) by the method of Bradford (63), with the microtiter plate protocol as described by manufacturer, using bovine serum albumin (BSA) as a standard.

Isoelectric Point Determination

Isoelectric point determination was done with the Phastsystem, isoelectric focusing gel 3–9 and silver stained according to methods described by manufacturer. Standards used were phycocyanin (4.45, 4.65, 4.75), β-lactoglobulin B (5.10), bovine carbonic anhydrase (6.00), human carbonic anhydrase (6.50), equine myoglobin (7.00), human hemoglobin A (7.10), human hemoglobin C (7.50), lentil lectin (7.8, 8.0. 8.2), cytochrome c (9.6), (IEF Standards pI range 4.45–9.6, BIO-RAD). After focusing, the gel was cut into 2 mm pieces and each incubated in 250 µl extraction buffer (50 mM Tris/HCl, 0.2 M NaCl, 1 mM DTT, 1 mM EDTA, 1% (v/v) glycerol, pH 8.0 overnight. Aliquotes of 5 µl were transferred to the assay mixtures, and activity measured using standard assay conditions.

Determination of pH/NaCl-optimum

Assays were done in a volume of 20 µl as described in standard assay using the PCR generated substrate and NaCl concentration from 0–200 mM with 25 mM intervals, and pH ranging from 9.5–6.5 with 0.5 pH unit intervals. All buffers were supplemented with 100 µg/ml BSA and 1 mM EDTA. The buffers used were diethanolamine/HCl (9.5–8.5), Tris/HCl (8.5–7.5) and MOPS/NaOH (7.5–6.5). All buffers were pH adjusted at 37° C. and used in 25 mM concentration in the assay.

Determination of Temperature Optimum

Assays were done in a volume of 20 µl as described in standard assay using the PCR generated substrate. The assay mixtures were as described in standard assay conditions and were adjusted to pH 8.0 for all temperatures. The temperature range used was 5° C. to 60° C. The activity was measured in a sequential manner with 15 min intervals, between each temperature. The enzymes used were diluted in standard dilution buffer (5 mM Tris/HCl, 10 mM NaCl, 1% (v/v) glycerol, pH 8.0) and placed on ice. Due to the instability of the enzyme sample on ice over a prolonged period, results were corrected with respect to the stability of the enzymes incubated in dilution buffer on ice, with the formula $N_{(t)}$–cpm/c$^{-0693(t/\lambda)}$, where half-life ($\lambda$) of cUNG and rhUNG are 2.0 hours and 2.6 hours respectively.

Effect of pH and Temperature on Stability pH: UNG (0.01 U) was preincubated (in a total volume of 75 µl) for 10 min at 37° in buffers containing 10 mM buffer, 10 mM NaCl, 1 mM EDTA, 1% glycerol, with pH ranging from 9.5–6.5 with 0.5 pH unit intervals using diethanolamine/HCl (9.5–8.5), Tris/HCl (8.5–7.5), MOPS/NaOH (7.5–6.5) and MES/NaOH (6.5–5.5) as buffer components. Aliquots of 5 µl were transferred to the assay mixtures and residual activity was measured using standard assay conditions.

Temperature: UNG (0.01 U) was preincubated (in a total volume of 75 µl) in 10 mM Tris/HCl, 50 mM NaCl, 1 mM EDTA, 1% glycerol, pH 8.0 (adjusted at each temperature). After different time intervals, as indicated in figure legends, 5 µl aliquots were transferred to the assay mixtures and residual activity was measured using standard assay conditions.

Substrate Specificity Against ss/ds DNA

PCR and nick-translated substrate was incubated 3 min at 100° C. and thereafter rapidly cooled on ice to generate ssDNA. Following denaturation, the ssDNA-substrates were used in standard assay condition with $6.65 \times 10^{-4}$ U purified cUNG. Enzyme activity was also measured using dsDNA substrates for both nick- and PCR-substrate, and used as references.

Ugi Inhibitor- and Uracil Product Inhibition

Activity measurements using PCR-substrate were performed with $6.65 \times 10^{-4}$ U of purified cUNG. Various concentrations of uracil (0, 1, 2 and 5 mM) or Ugi-inhibitor ($1.25 \times 10^3$ U to $2.00 \times 10^2$ U) were added to the assay mixtures (on ice). Activity was then measured as described under standard assay conditions.

Results

Purification of cUNG

Atlantic cod UNG was purified 17,000 fold with a recovery of 2%, as shown in table 1. Despite the high purification factor the enzyme was only partly purified, as determined by SDS-PAGE. Also the yield was low, due to many purification steps, and the concentration of the dilute protein sample before the gel-filtration step.

Molecular Weight and pI-determination

The molecular weight was determined by gel filtration to be 25 kD±2, from three separate experiments. The isoelectric point determination was done with an IEF Phast Gel with IEF standards ranging from 4.42–9.6. Following IEF, cUNG activity was eluted from the gel fragments and activity measured as described in material and methods.

cUNG activity co-eluted with the cytochrome c, standard with an isoelectric point of 9.6, as shown in FIG. 1. The cytochrome c and cUNG activity were found where the electrode contacted the gel, therefore we can only conclude that the pI is larger than 9.0, which is the highest measurable value using this system.

Substrate Specificity cUNG activity was measured using both ssDNA and dsDNA. A 1.8 and 1.9 fold higher activity for ssDNA than dsDNA was found using nick- and PCR-substrates, respectively, as shown in table 2. Assay products were analyzed by thin layer chromatography, and the major part of the radioactivity was identified as uracil. However, some radioactivity was also co-localized with the deoxyuridine marker, but this could be due to the partial overlap of the two markers. In addition the purified cUNG did not exhibit any significant hydrolysis of $^3$H-adenine-labelled DNA, therefore excluding nucleases as responsible for hydrolyzing the DNA.

Inhibition Studies

Figure 2:
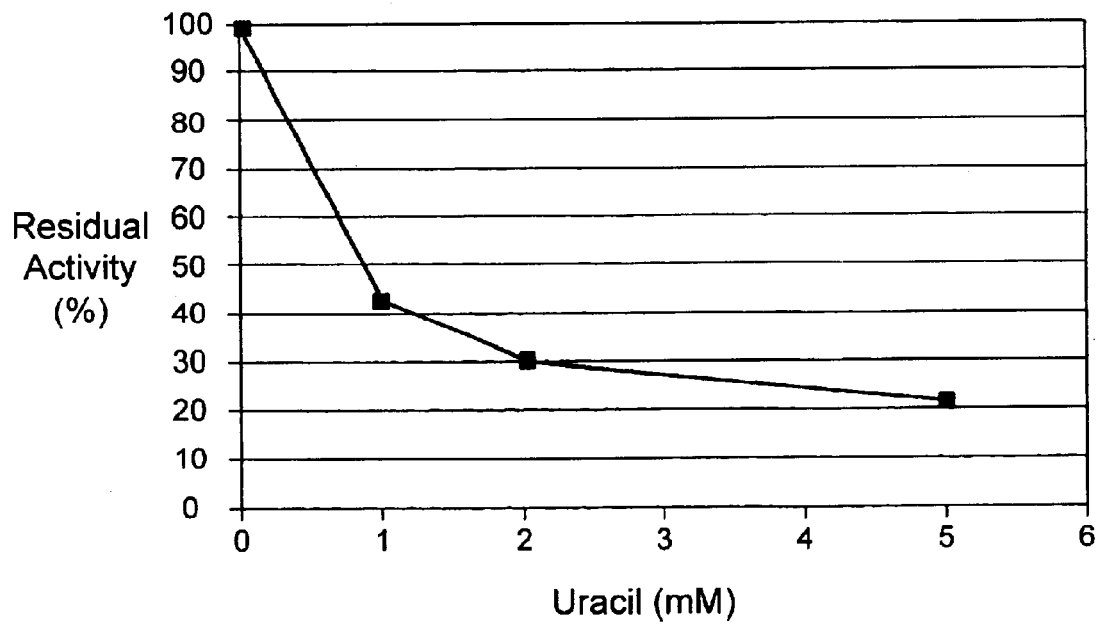
FIG. 2 shows product inhibition of cUNG with free uracil. Different concentrations of uracil was added to the assay mixture and the assay performed as described in material and methods.
Figure 3:
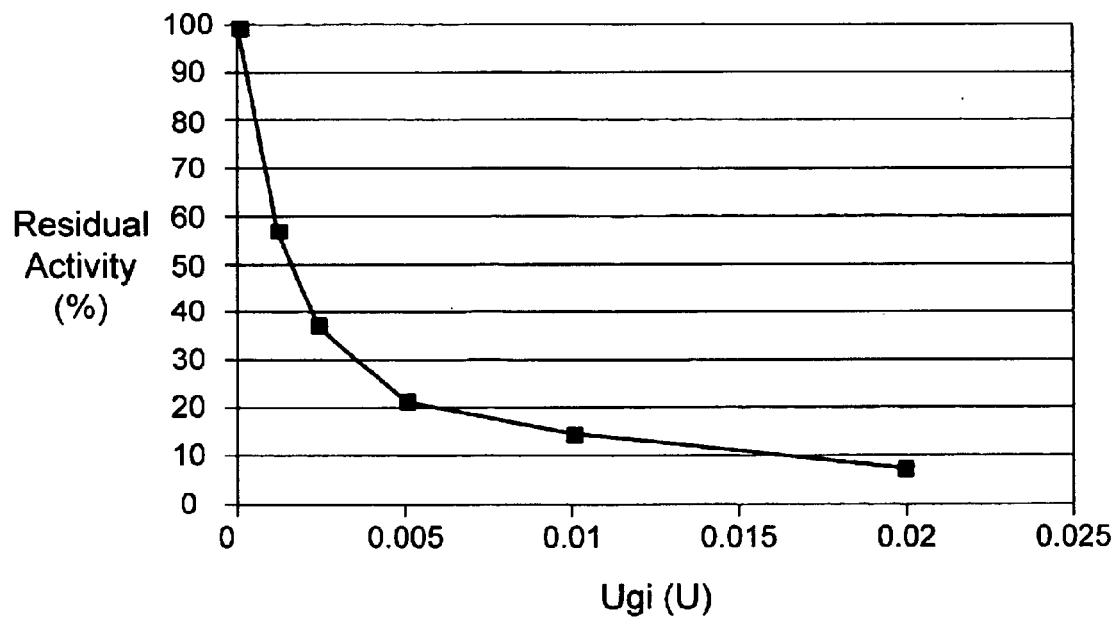
FIG. 3 shows inhibition of cUNG with the *Bacillus subtilis* bacteriophage uracil-DNA glycosylase inhibitor (Ugi). $6.65 \times 10^{-4}$ U of cUNG was incubated with $1.25 \times 10^3$ U to $2.00 \times 10^2$ U of Ugi using standard assay conditions, as described in material and methods. One Unit of Ugi inhibit one Unit of UNG-activity, where the UNG-activty is defined as releasing 60 pmol of uracil per min at 37° C.

Product inhibition by free uracil was examined, and gave more than 50% inhibition with 1 mM uracil in the assay mixture, as shown in FIG. 2. Adding 5 mM free uracil to the assay mixture, a 78% inhibition of the activity was observed. The effect of Ugi on cUNG was measured by adding Ugi to the assay mixture. cUNG was clearly inhibited by Ugi, as shown in FIG. 3.

pH and NaCl Optimum

Figure 4:
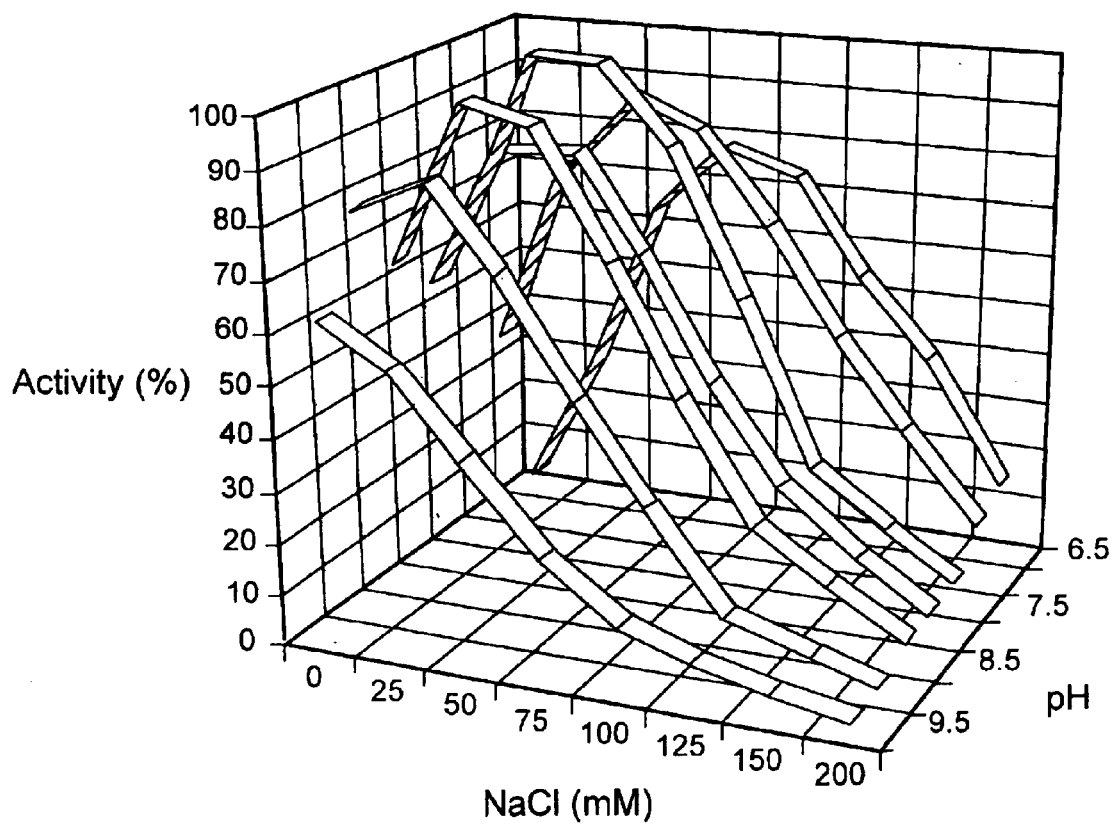
FIG. 4 shows pH and NaCl optimum of cUNG. Activity of cUNG was measured with variable sodium chloride concentrations in different pH-series, as described in material and methods. The percent UNG activity is set relative to the highest value measured, pH 7.5 with 50 mM NaCl.

The pH- and sodium chloride optimum was examined by measuring the enzyme-activity at different pHs using NaCl-concentration from 0–200 mM, as shown in FIG. 4. The enzyme exhibited a broad pH-optimum, with maximal activity between pH 7.0–9.0, and 25–50 mM NaCl. A shift in NaCl optimum was observed, where the optimum NaCl concentration changed from low concentrations at high pH to higher concentrations at low pH. At pH 9.5 cUNG was inhibited by NaCl.

Temperature Optimum

Figure 6:
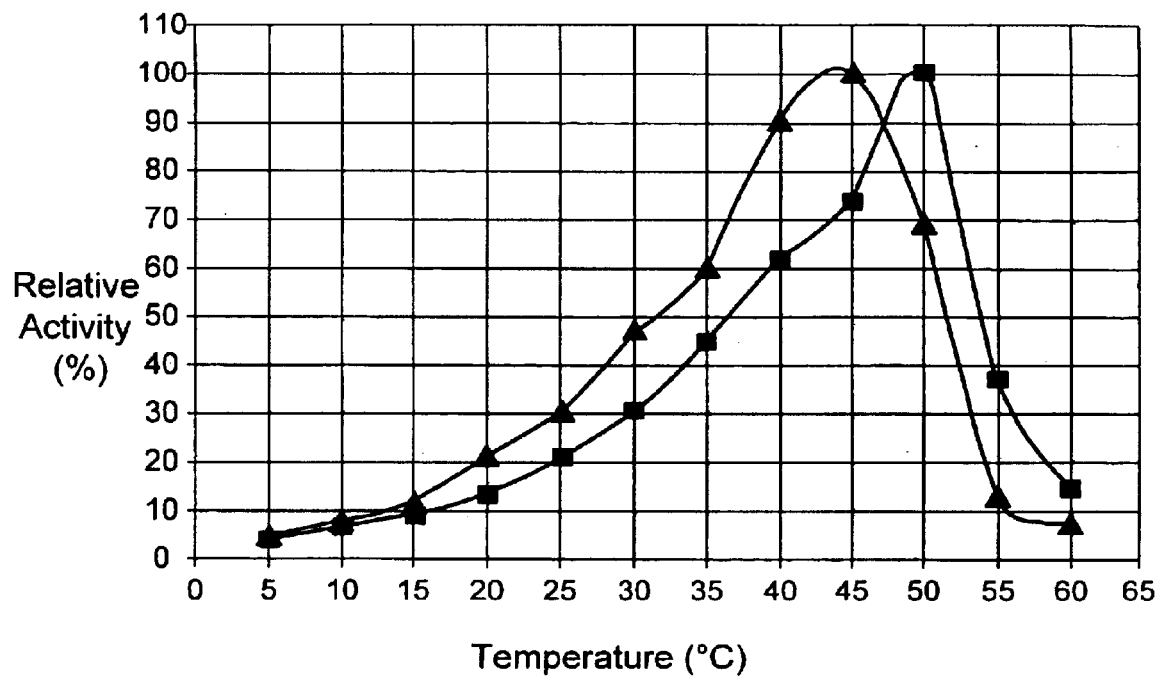
FIG. 6 shows Temperature profile of cUNG (Δ) and rhUNG (□). Enzyme activity was measured as described in material and methods. The percent UNG activity is set relative to the highest value for cUNG (45° C.) and rhUNG (50° C.) respectively. Due to prolonged incubation of the enzyme samples on ice during the experiment, activity is corrected with respect to the stability of the enzymes, as described in material and methods.

The temperature optimum of cUNG was determined to 41° C. (FIG. 5). To compare the activity of cUNG with the mesophilic rhUNG at low temperatures, enzyme activity was measured from 5–60° C., and the activity at low temperatures compared to their respective optimum temperature (FIG. 6). The activity profile of these two enzymes showed little difference at 5–15° C. However at temperatures from 20–40° C., a higher relative activity was observed with cUNG than rhUNG, whereas at high temperatures (50–60° C.) the opposite was observed.

Stability

Figure 7:
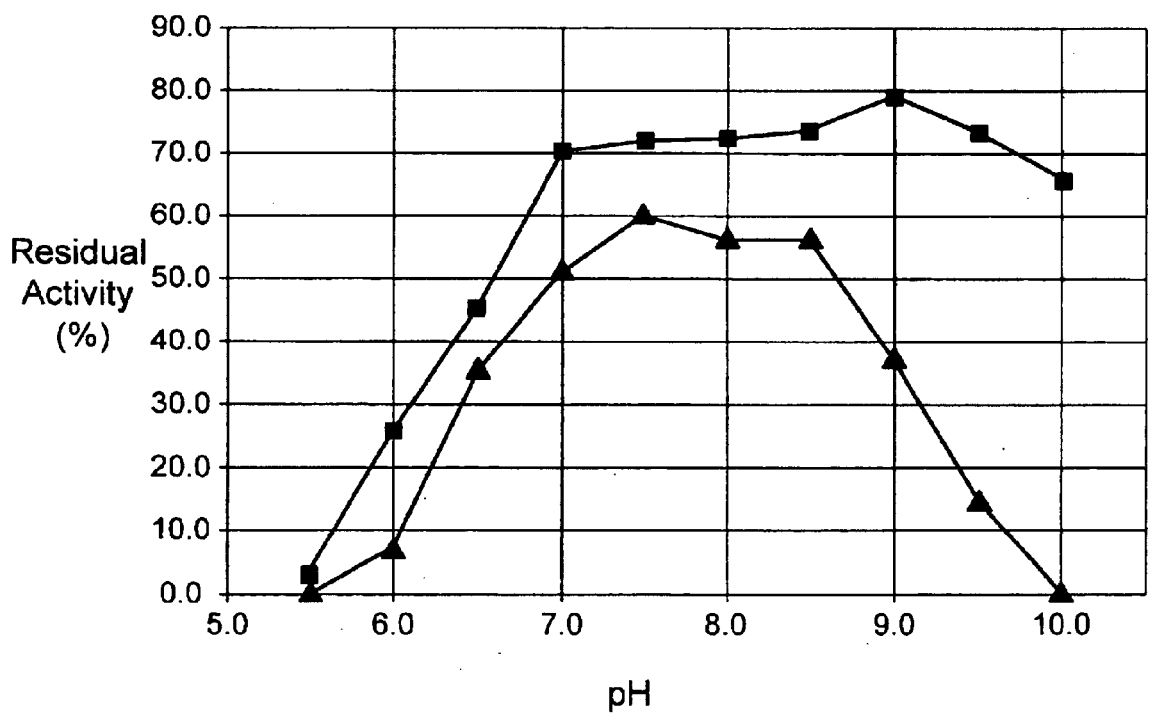
FIG. 7 shows pH stability of Atlantic cod UNG (cUNG) and recombinant human UNG (rhUNG). In the different pH-buffer, 1 U of cUNG (Δ) or rhUNG (□) were incubated for 10 minutes at 37° C. Then 5 µl aliquotes were transferred to the assay mixture, and residual activity was measured using standard assay conditions as described in materials and methods. One hundred percent activity was measured directly from a sample diluted at pH 8.0 without any incubation step.
Figure 8A:
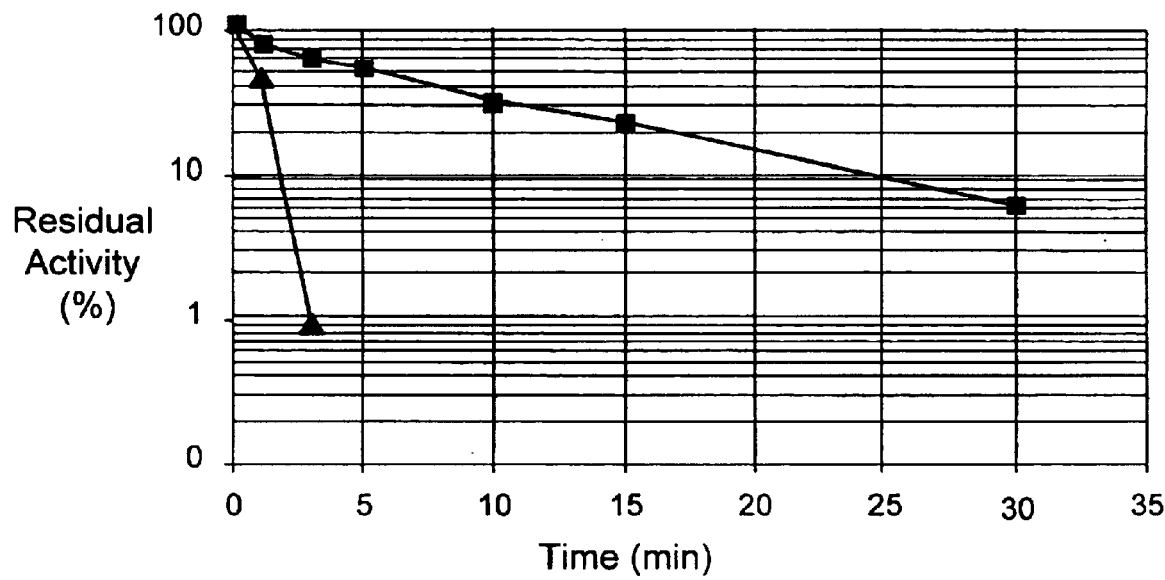
FIG. 8 shows temperature stability of Atlantic cod UNG (cUNG) (Δ) and recombinant human UNG (rhUNG) (□). Enzyme (1 U) were incubated at 50° C., 37° C., 25° C. and 4° C., and 5 µl aliquotes were transferred to the assay mixture after different time intervals, and standard assays were performed as described in material and methods. Half-lifes were determined to 0.5 min (50° C.), 20 min (37° C.), 60 min (25° C.) and 2 h (4° C.) for cUNG and 8 min (50° C.) 30 min (37° C.), 150 min (25° C.) and 2.6 h (4° C.) for rhUNG.
Figure 8B:
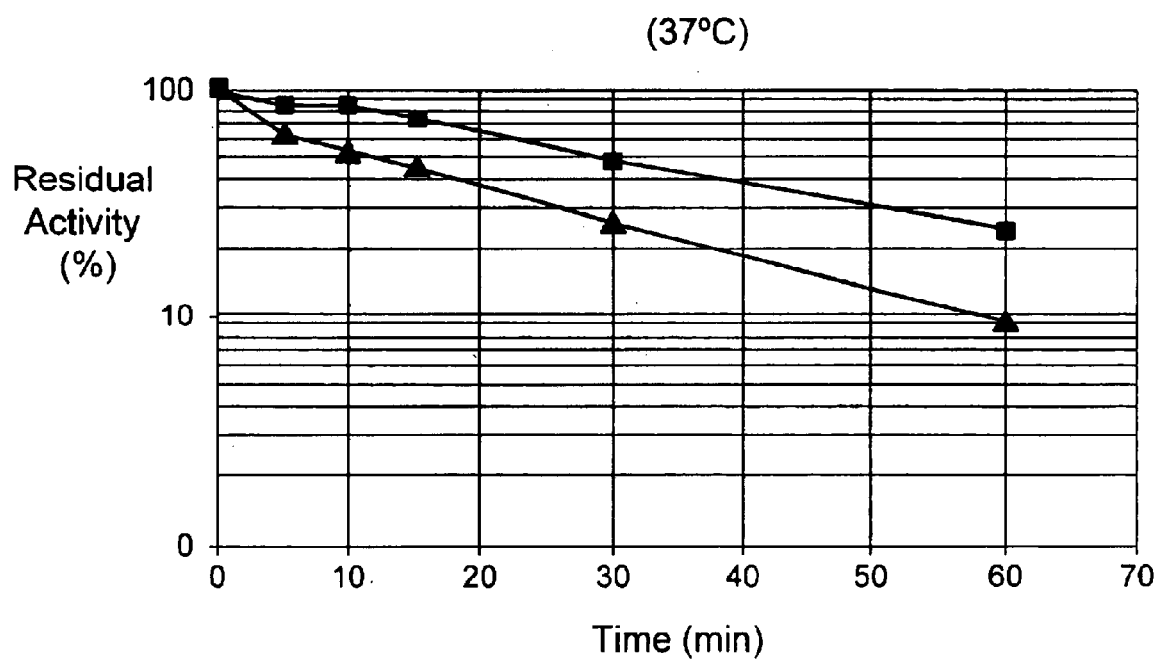
Figure 8C:
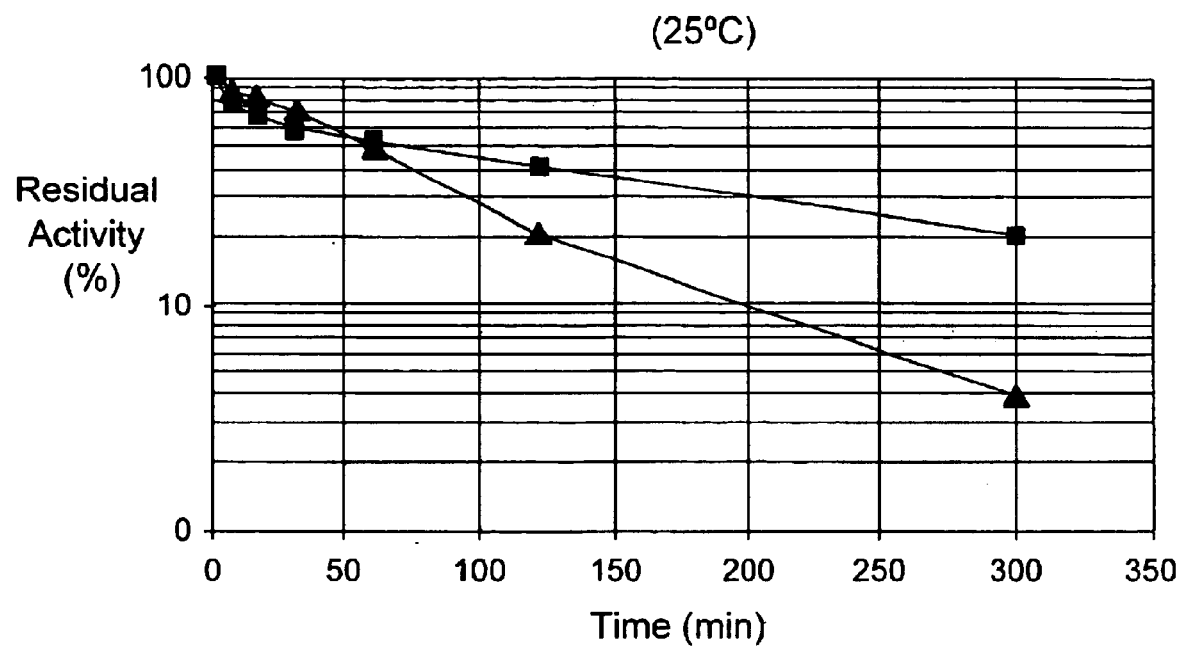
Figure 8D:
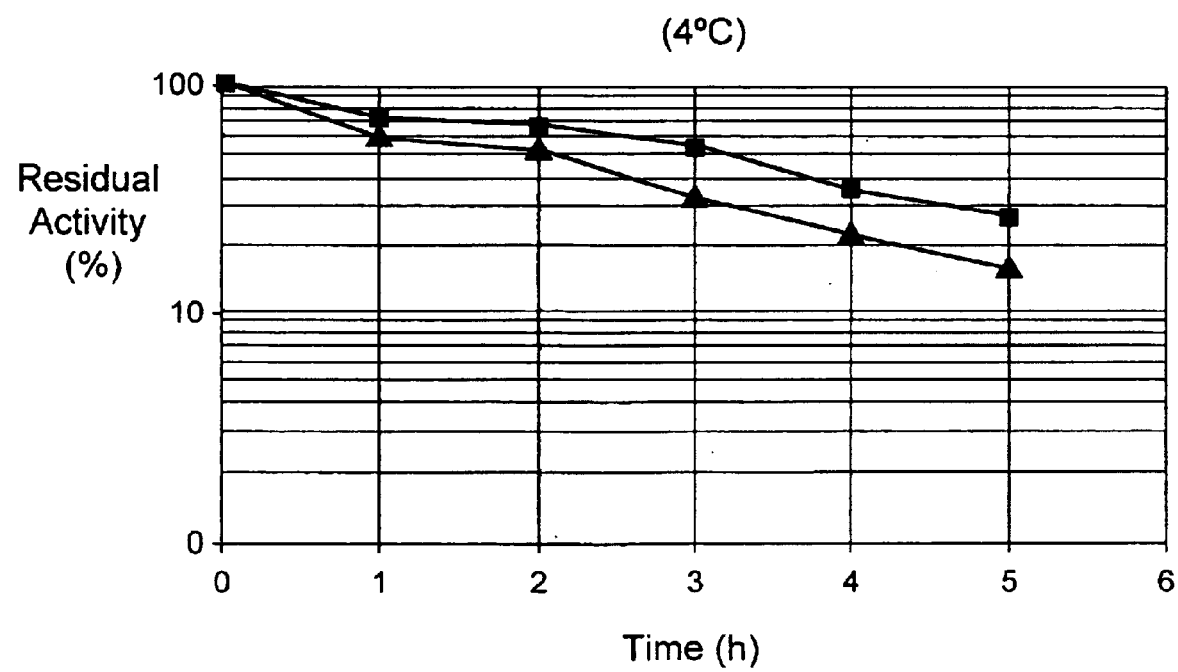

The stability of the two UNG enzymes were compared by preincubating the enzymes at different pHs. Atlantic cod UNG was shown to be most stable between pH 7.0–8.5. At pH 5.5 and pH 10.0 it had less than 1% residual activity. rhUNG was most stable between pH 7.0–9.5. At pH 5.5 3% residual activity remained, but at pH 10.0, as much as 66% of the activity remained, as shown in FIG. 7. The temperature stability of the two UNG-enzymes was compared at 4° C., 25° C., 37° C. and 50° C. At 50° C., the half-life was determined to be 0.5 min and 8 min for cUNG and rhUNG respectively. At all temperatures examined, rhUNG was more stable than cUNG. Half-lives determined were 20 min (37° C.), 60 min (25° C.) and 2 h (4° C.) for cUNG and 30 min (37° C.), 150 min (25° C.) and 2.6 h (4° C.) for rhUNG, but the largest difference in half-life was found at the highest temperature, as shown in FIG. 8.

Discussion

Purification and Molecular Weight

The uracil-DNA glycosylase from Atlantic cod liver (*Gadus morhua*) was purified 17,679 fold using several chromatographic techniques. Still the enzyme was only partly purified, as several other bands were seen on a SDS-PAGE gel. Human nuclear and mithochondrial uracil-DNA glycosylases are shown to be generated by alternate splicing, and have an ORF of 313 and 304 amino acids respectively (49). The molecular weight of cUNG was determined to 25 kD. This is approximately the same molecular weight as determined for the UNG from human placenta (29 kD) and the rhUNG (UNGAΔ84) (27 kD), which lacked 77 and 84 of the first N-terminal amino acids respectively, as predicted from the mithochondrial ORF (21, 64). This suggest that the N-terminal signal sequence in the purified cUNG is processed or artificially cleaved during purification or that Atlantic cod UNG does not have a N-terminal signal sequence. During purification we did not see any sign of two different UNGs as previously described during purification of UNG from rat or human sources (18, 23). But as a vertebrate, one should expect that Atlantic cod possesses both a nuclear and a mitochondrial form of UNG, but so far no effort has been given to reconcile this matter.

The uracil-DNA glycosylase from Atlantic cod was similar to other uracil-DNA glycosylases previously purified and characterized with respect to the high pI (19) and the two-fold preference to ssDNA than dsDNA (19).

Inhibition by Ugi and Uracil

The *Bacillus subtilis* bacteriophage PBS2 UDG-inhibitor (Ugi) inhibits UNG by forming a stable complex with UNG at physiological conditions). Ugi binds to human UNG by inserting a beta strand into the conserved DNA binding groove (67), and acts by mimicking DNA (68). This indicates that the structure of the substrate binding site of cUNG is similar to other UNGs inhibited by the Ugi-inhibitor. Inhibition with free uracil was in agreement with values previously reported (19).

Optimum Conditions cUNG was shown to have a broad pH optimum from 7.0–9.0, and the activity was strongly affected by NaCl-concentration. The broad optimum activity is previously reported for several other UNGs characterized (23, 31, 40, 47). Interestingly the NaCl-optimum for cUNG increases as pH decreases. It has previously been demonstrated that UNG functions in a processive manner at low ionic strength, which involves that when NaCl-concentration increases, the enzyme switches to a distributive mechanism (14, 15). However Purmal et al reported the opposite, that UNG acted in a distributive mechanism at low ionic strength. The processive mechanism is a common feature among several DNA interactive proteins (polymerases, repressors, restriction/modification enzymes, DNA repair enzymes), and the interactions are generally electrostatic in nature (67–71)]. In a UV-endonuclease from *Micrococcus luteus* the processive mechanism has also been shown to be pH-dependent (72). Therefore we suggest that the shift in NaCl-optimum with increasing pH reflects the processive/distributive nature of cUNG. And it could be that the controversy in the previous reports are also due to different buffer components and pH, in addition to the differences already discussed.

The temperature optimum (41° C.) was found to be slightly lower than the mesophilic rhUNG (45° C.) (64). The relative activity at temperature from 5–45° C. was higher for cUNG than rhUNG. At temperatures higher than 45° C., rhUNG shows a higher relative activity than cUNG, presumably as a consequence of the low temperature stability of cUNG.

Temperature and pH Stability

Enzymes characterized from cold-adapted species have been found to be more temperature and pH-labile, proposed due to their flexible structure in order to maintain enzymatic activity at low temperatures (73). cUNG was found to be both more pH- and temperature labile than the rhUNG, which are known features for other cold-adapted enzymes (73, 74).

A psychrophilic UNG from a marine bacterium has previously been isolated, and was compared to *E. coli* UNG with respect to temperature stability (45). This procaryotic UNG had a half-life of 2 min at 40° C. and 0.5 min at 45° C., compared to 27 and 8 min for the *E. coli* UNG. cUNG was compared to the rhUNG with respect to both temperature and pH stability. At 50° C. rhUNG had a half-life of 8 min, compared to 0.5 min for cUNG. At lower temperature the difference in half-life was less, although rhUNG was more stable than cUNG at all temperatures examined. Both enzymes were shown to be labile at low pH, whereas at high pH rhUNG was more stable than cUNG.

In conclusion, the uracil-DNA glycosylase from Atlantic cod was shown to be similar to other uracil-DNA glycosylases previously purified and characterized with respect to molecular weight, high pI, a broad pH-optimum and a two-fold preference to ssDNA than dsDNA. However the cUNG was shown to be more temperature and pH-labile and has a higher relative activity at low temperatures than the mesophilic rhUNG.

EXAMPLE 2

Isolation of the Uracil-DNA Glycosylase Gene from *Gadus morhua*

The following materials were used; SuperScript™ II Rnase H⁻ Reverse Transcriptase (Gibco BRL), Packagene® Lambda DNA packaging system was purchased from Promega (Madison, Wis.), Deoxy[5-$^3$H]urldine 5'-triphosphate (17.0 Ci/mmol) was purchased from Amersham (England), expression vector pTrc99A was purchased from Amersham Pharmacia Biotech (Uppsala, Sweden), restriction enzymes were purchased from New England Biolabs (Beverly, Mass.), SMART™ PCR cDNA Library Construction kit and Marathon™ cDNA Amplification Kit were purchased from Clontech (Palo Alto, Calif.). *Escherichia coli* NRB8052 [Δ(pro-lac), thi-, ara, trpE9777, ung1] (75, 76) and purified recombinant human UNG (UNGΔ84) (64) was provided by Dr. Hanis E. Krokan, Institute for Cancer Research and Molecular Biology, Norwegian University of Science and Technology.

Isolation of mRNA mRNA was isolated from 250 mg cod liver losing Oligotex direct mRNA Midi kit (Qiagen), following the instructions in manufacturers protocol.

Preparation of cDNA cDNA was made from 250 ng of the isolated poly A⁺ RNA using SMART™ PCR cDNA Library Construction kit (Clontech) according to the protocol recommended by the manufacturer. In brief, $1^{st}$ strand cDNA was made by combining 250 ng A+ RNA with 10 pmol SMART oligonucleotide (5'-TACGGCTGCGAG AAGACGACAGAAGGG-3') (SEQ ID NO:8) and 10 pmol CDS/3' PCR primer (Oligo(dT)30 N-1N (N=A, G, C, or T; N-1=A, G, C or T)) in a final volume of 5 μl, and incubated at 72° C. for 2 min and then placed directly on ice for 2 min to denature the RNA. Then enzyme and buffer were added to the reaction mixture to a final volume of 10 μl, consisting of 50 mM Tris/HCl. pH 8.3, 6 mM MgCl$_2$, 75 mM Kcl, 2mM DTT, 1 mM dATP, dCTP, dGTP and dTTP respectively and 200 U SuperScript™ II reverse transcriptase (Gibco BRL), and then incubated at 42° C. for 1 h. Synthesis of $2^{nd}$ strand was done by PCR in a final volume of 100 μl, containing 2 μl of the $1^{st}$ strand reaction as template, 40 mM Tricine/KOH pH 9.2 (25° C.), 15 mM KOAc, 3.5 mM Mg(OAc)$_2$, 3.75 μg/ml BSA, 0.2 mM of dATP, dCTP, dGTP and dTTP respectively, 1U Advantage cDNA Polymerase Mix (Clontech), 0.2 μM 5'-PCR primer (5'-TACGGCTCCGAGAAGACGACAGAA-3') (SEQ ID NO:9) and CDS/3'-PCR primer respectively.

PCR amplification was done in a GeneAmp 9700 thermocycler (Perkin Elmer), by 95° C. for 1 min followed by 16 cycles of 95° C. for 15 sec and 68° C. for 5 min.

ds cDNA polishing To 50 μl of the amplified ds cDNA, 40 μg proteinase K was added and incubated at 45° C. for 1 h. Proteinase K was inactivated by incubating the mixture at 90° C. for 8 min. To blunt end the ds cDNA, 15 U of T4 DNA polymerase was added and incubated at 16° C. for 30 min and 72° C. for 10 min. Finally the ds cDNA was ethanol precipitated and resuspended in 10 μl H$_2$O. All tubes were kept on ice if not otherwise stated.

Generation of a 300 bp Fragment of the cUNG-gene

Degenerated oligonucleotide primers were designed from two conserved regions (GQDPYH and VFLLWG) from known UNG- amino acid sequences. Codon usage for Atlantic cod were also considered when designing the primers. The UNG fragment was generated by PCR with cod liver cDNA as template in a final volume of 50 μl, containing 10 mM Tris/HCl pH 9.0 (25° C.), 50 mM KCl, 0.1% Triton X-100, 10 ng cDNA, 0.2 mM dATP, dCTP, dGTP and dTTP respectively, 2.0 μM upstream primer (5'-GGH-CAR-GAY-CCC-TAY-CA-3') (SEQ ID NO:10) and downstream primer (5'-DCC-CCA-SAG-SAG-RAA-VAC-3')[1] (SEQ ID NO:11) respectively and 2.5 U Taq-polymerase (Promega). PCR was carried out at 94° C. for 1 min, 60° C. for 1 min and 72° C. for 1 min, and a final extension step of 72° C. for 5 min.

The nucleotide symbols used are as follows; A=Adenine; C=Cytosine; G=Guanine; T=Thymine; D=A+G+T; R=A+G; S=C+G; V=A+C+G; Y=C+T DNA Sequencing DNA sequencing was done with the Amersham Pharmacia Biotech Thermo Sequenace Cy5 Dye Terminator Kit, ALFexpress™ DNA sequencer and ALFwin Sequence Analyzer version 2.10. Gels were made with Reprogel™ Long Read and Reprosel UV-polymerizer. All items were purchased from Amersham Pharmacia Biotech (Uppsala, Sweden).

RACE Procedure

Ligation of adaptors to cDNA was done as described in the protocol from the manufacturer. In brief, RACE-adaptors were ligated to cDNA in a total volume of 10 μl containing 50 mM Tris-HCl (pH 7.8), 10 mM MgCl$_2$, 10 mM DTT, 1 mM ATP, 0.75 μg cDNA, 2 μM Marathon cDNA adaptor (Clontech), 400 U T4 DNA ligase. The reaction was incubated at 16° C. for 16 h, and 5 min at 70° C. to inactivate the ligase. Before RACE, the adaptor ligated cDNA was diluted 50 times in TE-buffer and denatured at 100° C. for 2 min and placed directly on ice.

The sequence deduced from the 300 bp fragment of the UNG-gene was used to design two primers for both 3'- and 5'- rapid amplification of cDNA ends (RACE), with a small overlap region between the two fragments generated. Both 3'- and 5'- RACE reactions were done in a volume of 50 μl with 1 μl of diluted cDNA with RACE-adaptors as template, 0.2 μM internal 3'-(5'-TGTACCGACATTGATGGCTTCAAGCAT-3') (SEQ ID NO:12) or 5'-(5'-CCCATCCGCTTAGATCTCCATGTCCAG-3') (SEQ ID NO:13) RACE primers, respectively, 0.2 μM AP1-primer (supplied by manufacturer) (5'-CCATCCTAATACGACTCACTATAGGGC-3') (SEQ ID NO:14),40 μM Tricine/KOH pH 9.2 (25° C.), 15 mM KOAc, 3.5 mM Mg (OAc)$_2$, 3.75 μg/ml BSA, 0.2 mM of each dATP, dCTP, dGTP and dTTP and 10U Advantage cDNA Polymerase Mix (Clontech). Amplification was done in a Gene- Amp 9700 thermocycler (Perkin Elmer), 94° C. for 30 sec followed by 5 cycles of 94° C. for 5 sec and 72° C. for 3 mm, 5 cycles of 94° C. for 5 sec and 70° C. for 3 min, and 20 cycles of 94° C. for 5 sec and 68° C. for 3 min.

(Individual bands were purified from an agarose gel, and used as template in a new PCR-reaction with the same conditions as above to generate more DNA.)

Isolation of Two Different UNG Genes

Both RACE-fragments generated were sequenced using their respective internal RACE-primers.

Examining the sequence of the 5'-RACE-fragment indicated a double sequence, difficult to read, near the 5'-end of the fragment. However at the end of the fragment only one sequence appeared, due to a long UTR in one of the UNG-sequences but not the other. A new primer complementary to this 5'-end was designed (5'-ATGGAATTCGATTGAGATTGGCGCCTTTGG-3') (SEQ ID NO:12) and a new PCR-reaction was carried out with this, and the 5'-RACE internal primer, with the 5'-RACE fragment as template. The PCR was carried out in a final volume of 50 µl with 10 mM Tricine/KOH pH 9.2 (25°C.), 15 mM KOAc, 3.5 mM Mg(OAc)$_2$, 3.75 µg/ml BSA, 0.2 mM of dATP, dCTP, dGTP and dTTP respectively, 1U Advantage cDNA Polymerase Mix (Clontech), 10 ng cDNA as template and 0.2 µM upstream and downstream primers respectively. Amplification was done in a GeneAmp 9700 thermocycler (Perkin Elmer), 94°C. for 1 min. followed by 30 cycles of 94°C. for 30 sec, 60°C. for 1 min and 72°C. for 1 min.

The fragment was sequenced using the internal RAGE-primer, and the sequence was subtracted from the double sequence region described above. A primer complementary to the 5 p end of the underlying sequence was designed (consisting of both nucleotides from the SMART-sequence and the remaining UNG-sequence), and a PCR-reaction with this and the internal 5'-RACE-primer was carried out. The new fragment was sequenced as described above. From the two different UNG-sequences in the 5'-RACE-fragment, two final primers (UNG1 and UNG2) were made to isolate the full length UNG1 and UNG2, respectively, using cDNA as template and the same PCR-conditions as described above.

Construction of Expression Vectors

The catalytic domain of the UNG-gene was cloned in the expression vector pTrc99A, containing a strong trc promoter upstream of a multiple cloning site (77). Several different constructs were made by PCR-amplifying the gene using cDNA as template with upstream and downstream primers containing EcoRI and SalI restriction sites respectively. DNA-fragments were purified, digested with EcoRI and SalI and ligated into the pTrc99A expression vector. In brief, PCR-fragments with restriction sites were generated in a PCR-reaction (50 µl) containing 40 mM Tricine/KOH pH 9.2 (25° C.), 15 mM KOAc, 3.5 mM Mg(OAc)$_2$, 3.75 µg/ml BSA, 0.2 mM of dATP, dCTP, dGTP and dTTP respectively, 1U Advantage cDNA Polymerase Mix (Clontech), 10 ng cDNA as template and 0.2 µM upstream and downstream primers respectively. Amplification was done in a GeneAmp 9700 thermocycler (Perkin Elmer), 94° C. for 1 min followed by 30 cycles of 94° C. for 30 sec, 60° C. for 1 min and 72° C. for 2 min, and a final extension step of 72° C. for 5 min. Individual bands were purified from agarose gel, and used as template in a new PCR-reaction, with the same conditions as described above, to generate more DNA. DNA was purified using Quiaquick PCR purification kit (Millipore) as described by manufacturer, and eluted in TE-buffer, pH 8.0. Restriction enzyme digestion was done in a final volume of 30 µl containing 1 µg insert DNA or 0.25 µg pTrcr99A vector, 6 mM Tris/HCl, pH 7.9, 6 mM MgCl$_2$, 150 mM NaCl, 1 mM DTT (BufferD, Promega) and 3U of EcoRI and SalI. The mixtures were incubated at 37° C. for 3 h, followed by two times phenol/chloroform extraction, ethanol precipition and resuspended in 5 µl H$_2$O. Ligations were performed in a total volume of 10 µl containing 50 mM Tris-HCl (pH 7.8), 10 mM MgCl$_2$, 10 mM DTT, 1 mM ATP, 100 U T4 DNA ligase, 250 ng vector DNA and 1 µl insert DNA, and incubated at 16° C. for 16 h.

Competent *E. coli* JM105 (200 µl) was transformed with ligation mixes and grown on LB+ plates containing 100 µg/ml ampicillin at 37° C. Plasmid DNA was reisolated from positive clones and transformed in *E. coli* NR8052 used for expression of recombinant UNG.

Four different constructs were made rcUNGΔ74 and rcUNGΔ74o and rcUNGΔ81 and rcUNGΔ81o where 74 and 81 of the N-terminal amino acids were removed, respectively. These have the same length as the human Δ77 and Δ84, respectively (64). The Δ74o and the Δ81o constructs have the codons encoding arginine 87 and 88 optimized for expression in *E. coli*, by changing them from AGA to CGT. All constructs were made by PCR as described above, using the following primers and template:

```
rcUNGΔ74:
UDGL77 (5'-ACCATGGAATTCCCAAAAGCAACGCCTGCA-3')            (SEQ ID NO:13)
and
UDGEND2 (5'-GAGCTCGTCGACTTAGAGTGCCTCTCCAGTTTATAGG-3')   (SEQ ID NO:14)
and 10 ng cDNA as template.

rcUNGΔ81:
UDGL84 (5'-CCATGGAATTCTTCGGAGAGACTTGGAGAAGA-3')         (SEQ ID NO:15)
and
UDGEND2 and 10 ng cDNA as template.

rcUNGΔ74o:
(5'-ATGGAATTCGCAAAAGCAACGCCTGCAGGTTTCGGAGAGACTTGGCGTCGTCAC-3')  (SEQ ID NO:16)
and
UDGEND2 and 1 ng rcUNGΔ81o as template.

rcUNGΔ81o:
(5'-ATGGAATTCTTCGGAGAGACTTGGCGTCGTGAGCTGGCTGC-3')       (SEQ ID NO:20)
and
UDGEND2 and 10 ng cDNA as template.
```

Small Scale Expression of Uracil-DNA Glycosylase

Optimization of expression were done in 1 l baffled erlenmeyer flasks with 100 ml LB+ medium with 100 µg/ml ampicillin, inoculated with 5 ml of preculture. Cells were induced with 1 mM of IPTG at OD600=2.0, and induced at various length as indicated in figure legends. Expression was examined using various temperatures (20° C., 25° C., 30° C. and 37° C.).

The conditions above were also used to induce expression at various IPTG-concentrations (1 mM, 0.5 mM, 0.1 mM and 0.01 mM).

Fermentation Conditions

Fermentation was done in a 10 l Chemap CF 3000 fermentor (Switzerland). A 200 ml preculture of *E. coli* NR8052 with the pTrc99A oΔ84 construct was inoculated to 7 l of LB-medium supplemented with 20 mM glucose and 100 μg/ml ampicillin. Cells were grown to an OD600 of 2.0 and induced for 8 h with 1 mM IPTG. Additional glucose (3×50 ml of 20% glucose (W/v)) was supplemented during the fermentation to avoid glucose starvation. Cells were harvested and centrifuged at 10,000 g for 10 minutes. The cell paste was frozen at −70° C.

Purification of Recombinant Cod UNG Crude Extract

From the fermentation, 4 l of the *E. coli* NR8052 cells (68 g wet weight) were resuspended in 400 ml of extraction buffer (25 mM Tris/HCl, 10 mM NaCl, 1 mM EDTA, 1% glycerol, 1 mM DTT, 1 mM PMSF pH 8.0). The cells were disrupted by subjecting them five times through the Nebulizer using 100 psi of nitrogen. The extract was centrifuged 25,000 g for 10 min, and the supernatant removed. The pellet was resuspended in 100 ml of buffer A, and re-centrifuged as described above. The supernatants were combined and filtrated through glasswool (460 ml).

Protamine Sulphate

To the crude extract (460 ml), 60 ml of 2% protamine sulphate in buffer A (25 mM Tris/HCl, 10 mM NaCl, 1 mM EDTA, 1% glycerol, pH 8.0) was added and incubated at 4° C. for 5 min with stirring. The solution was centrifuged at 25,000 g for 10 min, and the supernatant was removed, 510 ml (fraction 1).

Q/S-sepharose

The protamine sulphate fraction was applied on a Q-sepharose column (5.0/10) coupled with a S-sepharose column (2.6/10), both equilibrated in buffer A, using a flow rate of 10 ml/min. Then the columns were washed with 750 ml buffer A, and the Q-sepharose column was then removed. The S-sepharose column was washed with an additional 550 ml buffer A+60 mM NaCl, and a gradient of 60 to 400 mM NaCl in buffer A was applied to elute the column, using a flow rate of 5 ml/min. Fractions of 10 ml were collected, and fractions containing UNG-activity were pooled (fraction 2, 115 ml).

Blue Sepharose FF

Fraction 2 was diluted two times in buffer A, and directly applied to a blue sepharose column (1.6/5.0), with a flow rate of 4 ml/min. The column was then washed with 30 ml of buffer A and 60 ml of buffer A+110 mM NaCl, and eluted with 60 ml buffer A+0.7 M NaCl. UNG containing fractions were pooled (fraction 3, 24 ml).

Superdex 75

Fraction 3 was concentrated to 3 ml using a Ultrafree 15 unit, (Millipore) and applied to the superdex 75 column (2.6/60) equilibrated in buffer A+0.15 M NaCl. A flow rate of 2 ml/min was used, and fractions of 5 ml were collected. Fractions containing UNG-activity were pooled (fraction 4, 30 ml).

Source 15Q

The Superdex 75 fraction was diafiltrated in an Ultrafree 15 unit (Millipore) and approximately ⅔ of the Superdex 75 fraction was applied to the Source 15Q column (2.6/3.0) equilibrated in buffer A at room temperature. The column was washed with 60 ml buffer A+60 mM NaCl, and then a gradient from 60 to 210 mM NaCl in buffer A was applied to elute the column. Fractions were collected on ice, and UNG-containing fractions were pooled (UNG-activity eluted between 105 to 145 mM NaCl).

Results

Nucelotide sequences as well as three-letter code amino acid sequences for cUNG1 and cUNG2, respectively are given in the enclosed Sequence listings, SEQ:ID:NOS 1 and 2.

Expression

Expression of rcUNG by the pTrc99A-Δ81o construct in 7 liter scale fermentation yielded a total of 413,480 Units of rcUNG contained in the crude extract.

Purification of Recombinant Cod UNG

Purification of recombinant cUNG (Δ81o) (rcUNG) is summarized in table 1. From a 4 l of the fermentation batch, 4.8 mg of recombinant UNG was purified to apparent homogeneity, and the molecular weight was determined to 28 kD by SDS-PAGE. The specific activity of the enzyme was determined to 30,092 U/mg using the nick-generated substrate with standard assay conditions. This preparation was found not to contain detectable levels of DNA-endodeoxy ribonucleases or—exodeoxy ribonucleases according to standard methods.

EXAMPLE 3

Measurement of Residual Activity/Reactivation After Thermal Inactivation 11.5 Units of rcUNG (approximately 0.38 μg) in 50 μl "Taq-buffer" (10 mM tris-HCl (pH=9.0 at 25 ° C.), 50 mM KCl, 0.1% Triton X-100) was inactivated for 10 min at 94° C., and divided into two equal parts. One part was kept at 4° C. and the other part was kept at 25° C. before residual activity was measured at 1 and 16 hours after inactivations using 15 μl undiluted inactivated mixture in a standard assay. Before inactivation, 2 μl was taken out and diluted 1:2000 before measuring the activity (100% control). The results showed that the inactivated enzyme did not cause release of radio labelled uracil from the substrate that was above the detection limit (blank control+2×standard deviation). At these conditions, the 100% control would yield 7,000,000 cpm, while 2× background standard deviation was 46 cpm. Consequently, the residual activity of rcUNG was less than 0.0006% of initial activity after thermal inactivation at these conditions. There was neither any significant reactivation of the enzyme after 16 hours at either 4° C. or 25° C.

The results show that rcUNG has no practical residual activity after thermal inactivation and that it does not reactivate. The enzyme rcUNG is therefore different from the previously isolated UNG from the marine bacterium, BMTU (45) which was shown to have a small degree of reactivation or residual activity after thermal inactivation.

EXAMPLE 4

Carry-over Prevention

It is tested whether cUNG is effective to degrade contaminating uracil-containing DNA in a carry-over prevention reaction.

Method

As a contaminant, 0.5 ng of uracil containing template DNA (761 bp fragment generated from cationic trypsinogen from Atlantic salmon (*Salmo salar*) (61) was added to the PCR-mix in a final volume of 50 μl, containing 10 mM Tris/HCl pH 9.0 (25° C.), 50 mM KCl, 0.1% Triton X-100, 10 ng cDNA, 0.2 mM dATP, dCTP, dGTP and dTTP respectively, 2.0 μM upstream-(OP5) and downstream primer (NP2) respectively and 1.0 U Taq-polymerase (Promega). UNG ($4 \times 10^{-3}$ or $1.7 \times 10^{-2}$ U) was added to the PCR-mix and incubated at ambient temperature (RT) for 10 minutes.

As negative controls, one PCR reaction mixture contained template with thymidine replacing uracil, and in one mixture water replaced UNG. Also, as a positive control $1.7\times10^{-3}$ U UNG from *E. coli* was used, instead of rcUNG.

Then PCR was carried out by 94° C. for 4 min, 30 cycles of 94° C. for 1 min, 60° C. for 1 min and 72° C. for 1 min. After the PCR the products were analyzed by agarose gel electrophoresis.

PCR Primer Sequences

```
OP5:  5'-TCTCTCGAGAAAAGAGAGGCTGAAGCTCCCATTGACGATGAGGATGA-3'  (SEQ ID NO:21)

NP2:  5'-GTAGAATTCGGATCCATGTCTCCTCCAGTCTAGAT-3'              (SEQ ID NO:22)
```

Result

Figure 9:
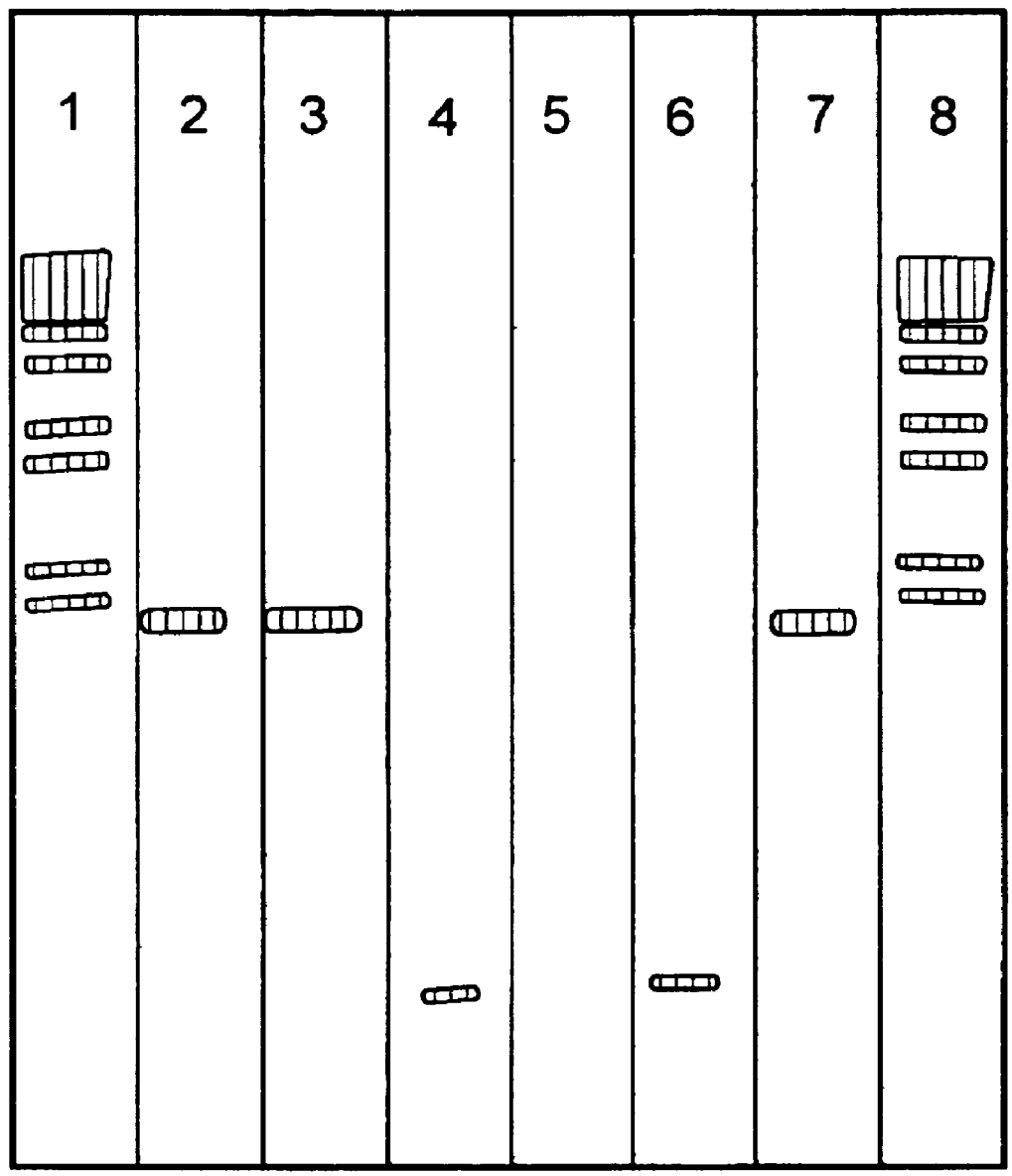
FIG. 9 shows agarose gel showing PCR products from carry over prevention test using recombinant Cod UNG (rcUNG). Lane descriptions: lanes 1 and 8: DNA ladder; lane 2: T-containing template, no UNG; lane 3: T-containing template, $1.7 \times 10^{-3}$ U rcUNG; lane 4: U-containing template, $4 \times 10^{-4}$ U rcUNG; lane 5: U-containing template, $1.7 \times 10^{-3}$ U rcUNG; lane 6: U-containing template, $4 \times 10^{-4}$ U *E. coli* UNG; lane 7: U-containing template, no UNG.

The result of the experiment according to the example is shown in FIG. 9. The uracil-containing templates were degraded by UNG in all PCR reactions while the reactions either without UNG or with thymine-containing templates yielded the expected PCR product. The results in FIG. 9 are shown as a figure of an agarose gel. The results show that rcUNG is effective to degrade contaminating uracil-containing DNA in a PGR reaction.

reaction cycles there is no detectable residual enzyme after heat treatment. Then there will be no unwanted degradation of the DNA product in the upscaling reaction by residual UDG enzyme activity and of course there will be no need to add enzyme inhibitor to avoid degradation of DNA by such residual UDG enzyme activity.

It is shown that the recombinant cUNG (rcUNG) has the same qualities/functions as the cUNG isolated from cod liver. Cod liver contains only small amounts of cUNG.

When cUNG is produced recombinantly, larger quantities of cUNG can be made compared to the amount of cUNG produced by extraction from cod liver.

REFERENCES

1. Lindahl, T., *An N-glycosidase from Eschorichia coli that releases free uracil from DNA containing deaminated cytosine residues.* Proc Natl Acad Sci, USA, 1974. 71(9): p. 3649–53.

TABLE 1

Purification of Atlantic cod liver uracil-DNA glycosylase (rcUNG).

| Step | Volume (ml) | Activity[a] (U/ml) | Total activity (U) | Protein conc (mg/ml)[b] | Total protein (mg) | Specific activity (U/mg) | Yield (%) | Purification Fold |
|---|---|---|---|---|---|---|---|---|
| Crude extract | 2000 | 0.086 | 172 | 4 | 8000 | 0.021 | 100 | 1 |
| Q-Sepharose FF | 2340 | 0.073 | 170 | 1.66 | 3884 | 0.044 | 99 | 2 |
| S-Sepharose FF | 55 | 1.795 | 98.8 | 0.155 | 8.53 | 11.6 | 58 | 540 |
| Heparin Sepharose | 20 | 2.775 | 55.5 | 0.081 | 1.62 | 34.3 | 32 | 1597 |
| Poly-U Sepharose | 70 | 0.446 | 31.2 | ND[c] | ND | ND | 18 | ND |
| Superdex75 | 3 | 1.138 | 3.41 | 0.003 | 0.009 | 379 | 2 | 17679 |

[a]Enzyme activity was measured as described under standard assay in material and methods using nick-substrate, in Example 2.
[b]Protein concentration was determined as described in material and methods.
[c]Protein concentration was to low to determine.

TABLE 2

Substrate specificity ssDNA versus dsDNA.

| Substrate | cpm | % activity | Fold |
|---|---|---|---|
| dsNick | 586 | 54 | 1.0 |
| ssNick | 1078 | 100 | 1.8 |
| dsPCR | 1158 | 52 | 1.0 |
| ssPCR | 2214 | 100 | 1.9 |

The present results show for the first time isolation, and use in carry-over prevention in DNA copying reactions, of an UNG from a cold-adapted eukaryotic organism. The previously known UNG enzymes isolated from *E. coli* (60) or BMTU (45), for use in PCR reactions are of prokaryotic origin.

The cUNG is completely inactivated when heated above 60° C. and the deactivation is completely irreversible (as there is no detectable residual enzyme after heat treatment). This quality makes cUNG a better candidate as an enzyme for use in carry-over prevention in DNA-copying reactions (PCR, LCR etc.) compared to enzymes previously known in this field, as *E. coli* UNG or UNG from BMTU, which were not completely and irreversibly inactivated after heat treatment. Because of the complete and irreversible deactivation of cUNG by the heat treatment normally performed in PCR 2. Lindahl, T., *DNA glycosylases, endonucleases for apurinic/apyrimidinic sites, and base excision-repair.* Prog Nucleic Acid Res Mol Biol, 1979.22: p. 135–92.
3. Kubota, Y., et al., *Reconstitution of DNA base excision-repair with purified human proteins: interaction between DNA polymerase beta and the XRCC1 protein.* Embo J., 1996. 15(23): p. 6662–70.
4. Nicholl, I. D., K. Nealon, and M. K. Kenny, *Reconstitution of human base excision repair with purified proteins.* Biochemistry, 1997. 36(24): p. 7557–66.
5. Parikh, S. S., C. D. Mol, and J. A. Tainer, *Base excision repair enzyme family portrait: integrating the structure and chemistry of an entire DNA repair pathway.* Structure, 1997. 5(12): p. 1543–50.
6. Slupphaug, G., et al., *Cell cycle regulation and in vitro hybrid arrest analysis of the major human uracil-DNA glycosylase.* Nucleic Acids Res., 1991. 19(19): p. 5131–7.
7. Muller, S. J. and S. Caradonna, *Isolation and characterization of a human cDNA encoding uracil-DNA glycosylase.* Biochim. Biophys. Acta, 1991. 1088(2): p. 197–207.
8. Muller Weeks, S. J. and S. Caradonna, *Specific association of cyclin-like uracil-DNA glycosylase with the proliferating cell nuclear antigen.* Exp. Cell Res., 1996. 226(2): p. 346–55.
9. Haushalter, K. A., et al., *Identification of a new uracil-DNA glycosylase family by expression cloning using synthetic inhibitors.* Curr. Biol., 1999. 9(4): p. 174–86.

10. Gallinari, P. and J. Jiricny, *A new class of uracil-DNA glycosylases related to human thymine-DNA glycosylase.* Nature, 1996. 383(6602): p. 735–8.
11. Barrett, T. E., et al., *Crystal structure of a G:T/U mismatch-specific DNA glycosylase: mismatch recognition by complementary-strand interactions.* Cell, 1998. 92(1): p. 117–29.
12. Sandigursky, M. and W. A. Franklin, *Thermostable uracil-DNA glycosylase from Thermotoga maritima a member of a novel class of DNA repair enzymes.* Curr. Biol., 1999. 9(10): p. 531–4.
13. Krokan, H. E., R. Standal, and G. Slupphaug, *DNA glycosylases in the base excision repair of DNA.* Biochem. J., 1997. 325(Pt 1): p. 1–16.
14. Higley, M. and R. S. Lloyd, *Processivity of uracil DNA glycosylase.* Mutat. Res. 1993. 294(2): p. 109–16.
15. Bennett, S. E., R. J. Sanderson, and D. W. Mosbaugh, *Processivity of Escherichia coli and rat liver mitochondrial uracil-DNA glycosylase is affected by NaCl concentration.* Biochemistry, 1995. 34(18); p. 6109–19.
16. Purmal, A. A., et al., *Uracil DNA N-glycosylose distributively interacts with duplex polynucleotides containing repeating units of either TGGCCAAGCU or TGGCCAAGCTTGGCCAAGCU.* J. Biol. Chem., 1994. 269(35): p.22046–53.
17. Colson, P. and W. G. Verly, *Intracellular localization of rat-liver uracil-DNA glycosylase. Purification and properties of the chromatin enzyme.* Eur. J. Biochem., 1983. 134(3): p. 415–20.
18. Domena, J. D. and D. W. Mosbaugh, *Purification of nuclear and mitochondrial uracil-DNA glycosylase from rat liver: Identification of two distinct subcellular forms,* Biochemistry, 1985. 24(25): p. 7320–8.
19. Domena, J. D., et al., *Purification and properties of mitochondrial uracil-DNA glycosylase from rat liver,* Biochemistry, 1988. 27(18): p. 6742 51.
20. Seal, G. P. Arenaz, and M. A. Sirover, *Purification and properties of the human placental uracil DNA glycosylase.* Biochem. Biophys. Acta., 1987. 925(2): p. 226–33.
21. Wittwer, C. U., G. Bauw, and H. E. Krokan, *Purification and determination of the $NH_2$-terminal amino acid sequence of uracil-DNA glycosylase from human placenta.* Biochemistry, 1989. 28(2): p. 780–4.
22. Krokan, H. and C. U. Wittwer, *Uracil DNA-glycosylase from HeLa cells: general properties, substrate specificity and effect of uracil of analogs.* Nucleic Acids Res., 1981. 9(11): p. 2599–613.
23. Wittwer, C. U. and H. Krokan, *Uracil-DNA glycosylase in HeLa S3 cells: interconvertibility of 50 and 20 kDa forms and similarity of the nuclear and mitochondrial form of the enzyme,* Biochim. Biophys. Acta., 1985. 832(3): p. 308–18.
24. Myrnes, B. and C. U. Wittwer, *Purification of the human O6-methylguanine-DNA methyltransferase and uracil-DNA glycosylase, the latter to apparent homogeneity.* Eur. J. Biochem. 1988. 173(2): p. 383–7.
25. Caradonna, S., et al., *Affinity purification and comparative analysis of two distinct human uracil-DNA glycosylases.* Exp. Cell Res., 1996. 222(2): p. 345–59.
26. Muller-Weeks, S., B. Mastran, and S. Caradonna, *The nuclear isoform of the highly conserved human uracil-DNA glycosylase is an Mr 36,000 phosphoprotein.* J. Biol. Chem., 1998. 273(34): p. 21909–17.
27. Seal. G., R. J. Tallarida, and M. A. Slrover, *Purification and properties of the uracil DNA glycosylase from Bloom's syndrome.* Biochim. Biophys. Acta., 1991. 1097 (4): p. 299–308.
28. Caradonna, S. J. and Y. C. Cheng, *Uracil DNA-glycosylase. Purification and properties of this enzyme isolated from blast cells of acute myelocytic leukemia patients.* J. Biol. Chem., 1980. 255(6): p. 2293–300.
29. Talpaert-Borle, M., L. Clerici, and F. Campagnari, *Isolation and characterization of a uracil-DNA glycosylase from calf thymus.* J. Biol. Chem., 1979. 254(14): p. 6387–91.
30. Talpaert-Borle, M., F. Campagnari, and D. M. Creissen, *Properties of purified uracil-DNA glycosylase from calf thymus. An in vitro study using synthetic DNA-like substrates.* J. Biol. Chem., 1982. 257(3); p. 1208–14.
31. Guyer, R. B., J. M. Nonnemaker, and R. A. Deering, *Uracil-DNA glycosylase activity from Dictyostelium discoideum.* Biochim. Biophys. Acta., 1986. 868(4): p. 262–4.
32. Crosby, B., et al., *Purification and characterization of a uracil-DNA glycosylase from the yeast. Saccharomyces cerevisiae.* Nucleic Acids Res., 1981. 9(21): p. 5797–809.
33. Blaisdell, P. and H. Warner, *Partial purification and characterization of a uracil-DNA glycosylase from wheat germ.* J. Biol. Chem., 1983. 258(3): p. 1603–9.
34. Talpaert-Borle, M. and M. Liuzzi, *Base-excision repair in carrot cells. Partial purification and characterization of uracil-DNA glycosylase and apurinic/apyrimidnic endodeoxyribonuclease.* Eur. J. Biochem., 1982. 124(3): p. 435–40.
35. Birch, D. J. and A. G. McLennan, *Uracil-DNA glycosylase in developing embryos of the brine shrimp (Artemia salina).* Biochem. Soc. Trans., 1980. 8(6): p. 730–1.
36. Lindahl, T., et al., *DNA N-glycosidases: properties of uracil-DNA glycosidase from Escherichia coli.* J. Biol. Chem., 1077. 252(10): p. 3286–94.
37. Cone, R., et al., *Partial purification and characterization of a uracil DNA N-glycosidase from Bacillus subtilis.* Biochemistry, 1977. 16(14), p. 3194–201.
38. Williams, M. V. and J. D. Pollack, *A mollicute (mycloplasma) DNA repair enzyme: purification and characterization of uracil-DNA glycosylase.* J. Bacteriol., 1990. 172(6): p. 2079–85.
39. Kaboev, O. K., et al., *Uracil-DNA glycosylase from Bacillus stearothermophilus.* FEBS Lett., 1981. 132(2): p. 337 40.
40. Purnpatre, K. and U. Varshney, *Uracil DNA glycoylase from Mycobacterium smegmatis and its distinct biochemical properties.* Eur J Biochem., 1998. 256(3): p. 580–8.
41. Kaboev, O. K., L. A. Luchkina, and T. I. Kuziakina, *Uracil-DNA glycosylase of thermophilic Thermothrix thiopara.* J Bacteriol, 1985. 164(1): p. 421–4.
42. Masters, C. I., B. E. Moseley, and K. W. Minton, *AP endonuclease and uracil DNA glycosylase activities in Deinococcus radiodurans.* Mutat. Res., 1991. 254(3): p. 263–72.
43. Koulis, A., et al., *Uracil-DNA glycosylase activities in hyperthermophilic micro-organisms.* FEMS Microbiol. Lett., 1996. 143(2–3): p. 267–71.
44. Leblanc, J. P., et al., *Uracil-DNA glycosylase. Purification and properties of uracil-DNA glycosylase from Micrococcus luteus.* J Biol Chem, 1982. 257(7): p. 3477–83.
45. Sobek, H., et al., *Heat-labile uracil-DNA glycosylase: purification and chararcterization.* FEBS Lett, 1996. 388 (1): p. 1–4.
46. Focher, F., et al., *Herpes simplex virus type 1 uracil-DNA glycosylase: isolation and selective inhibition by novel uracil derivatives.* Biochem J., 1993. 292(Pt 3): p. 883–9.

47. Winters, T. A. and M. V. Williams, *Purification and characterization of the herpes simplex virus type 2-encoded uracil-DNA glycosylase*. Virology, 1993. 195 (2): p. 315–26.
48. Slupphaug, G., et al., *Nuclear and mitochondrial forms of human uracil-DNA DNA glycosylase are encoded by the same gene*. Nucleic Acids Res., 1993. 21(11): p. 2579–84.
49. Nilsen, H., et al., *Nuclear and mitochondrial uracil-DNA glycosylases are generated by alternative splicing and transcription from different positions in the UNG gene*. Nucleic Acids Res., 1997. 25(4); p. 750–5.
50. Bharati, S., et al., *Human mitochondrial uracil-DNA glycosylase preform (UNG 1) is processed to two forms one of which is resistant to inhibition by AP sites*. Nucleic Acids Res., 1998. 26(21): p. 4953–9.
51. Haug, T., et al., *Regulation of expression of nuclear and mitochondrial forms of human uracil-DNA glycosylase*. Nucleic Acids Res., 1998. 26(6): p. 1449–57.
52. Otterlei, M., et al., *Nuclear and mitochondrial splice forms of human uracil-DNA glycosylase contain a complex nuclear localisaton signal and a strong classical mitochondrial localisation signal, respectively*. Nucleic Acids Res., 1998. 26(20): p. 4611–7.
53. Mol, C. D., et al., *Crystal structure and mutational analysis of human uracil-DNA glycosylase: structural basis for specificity and catalysis [see comments]*. Cell, 1995. 80(6): p. 869–78.
54. Savva, R., et al., *The structural basis of specific base-excision repair by uracil-DNA glycosylase*. Nature, 1905. 373(6514): p. 487–93.
55. Ravishankar, R., et al., *X-ray analysis of a complex of Eschorichia coli uracil DNA glycosylase (EcUDG) with a proteinaceous inhibitor. The structure elucidation of a prokaryotic UDG*. Nucleic Acids Res., 1998. 26(21): p. 4880–7.
56. Slupphaug, G., et al., *A nucleotide-flipping machanism from the structure of human uracil-DNA glycosylase bound to DNA [see comments]*. Nature, 1996. 384(6604): p. 87–92.
57. Parikh, S. S., et al., *Base excision repair initiation revealed by crystal structures and binding kinetics of human uracil-DNA glycosylase with DNA*. Embo J., 1998. 17(17): p. 5214–26.
58. Feller, G. and C. Gerday, *Psychrophilic enzymes: molecular basis of cold adaptation*. Cell Mol. Life Sci., 1997. 53(10): p. 830–41.
59. Kwok S. Higuchi R., Nature 1989, 339:237–8.
60. Longo M C, Berningr M S, Hartley J L, Gene 1990, 93:125–8.
61. Male, R., et al., *Molecular cloning and characterization of anionic and cationic varants of trypsin from Atlantic salmon*. Eur. J. Biochem., 1995. 232(2). p. 677–85.
62. Wang, K. T. and I. S. Wang, *Polyamide-layer chromatography of nucleic acid bases and nucleosides*. Biochim. Biophys. Acta., 1967. 142(1): p. 280–1.
63. Bradford, M. M., *A rapid and sensitive method for the quantitation of microgram quantities of protein utilizing the principle of protein-dye binding*. Anal. Biochem., 1976. 72: p. 248–54.
64. Slupphaug, G., et al., *Properties of a recombinant human uracil-DNA glycosylase from the UNG gene and evidence that UNG encodes the major uracil-DNA glycosylase*. Biochemistry, 1995. 34(1): p. 128–38.
65. Bennett, S. E., M. I. Schimerlik, and D. W. Mosbaugh, *Kinetics of the uracil-DNA glycosylase/inhibitor protein association. Ung interaction with Ugl, nucleic acids, and uracil compounds*. J Biol Chem, 1993. 268(36): p. 26879–85.
66. Karran, P., R. Cone, and E. C. Friedberg, *Specificity of the bacteriophage PBS2 induced inhibitor of uracil-DNA glycosylase*, Biochemistry, 1981. 20(21): p. 6092–6.
67. Mol, C. D., et al., *Crystal struture of human uracil-DNA glycosylase in complex with a protein inhibitor: protein mimicry of DNA*. Cell, 1995. 82(5); p. 701–8.
68. Savva. R. and L. H. Pearl, *Nucleotide mimicry in the crystal structure of the uracil-DNA glycosylase-uracil glycosylase inhibitor protein complex*. Nat Struct Biol, 1995. 2(9): p. 752–7.
69. Lohman, T. M., *Kinetics of protein-nucleic acid interactions: use of salt effects to probe mechanisms of interaction*. CRC Crit. Rev. Biochem., 1986. 19(3): p. 191–245.
70. von Hippel, P. H. and O. G. Berg, *Facilitated target location in biological systems*. J. Biol. Chem., 1989. 264(2); p. 675–8.
71. Dodson, M. L., M. L. Michaels, and R. S. Lloyd, *United catalytic mechanism for DNA glycosylases*. J. Biol. Chem., 1994. 269(52): p. 32709–12.
72. Hamilton, R. W. and R. S. Lloyd, *Modulation of the DNA scanning activity of the Micrococcus luteus UV endonuclease*. J. Biol. Chem., 1989. 264(29): p. 17422–7.
73. Outzen, H., et al., *Temperature and pH sensitivity of trypsins from Atlantic salmon (Salmo salar) in comparison with bovine and porcine trypsin*. Comp Biochem Physiol B Biochem. Mol. Biol., 1996. 115(1); p. 33–45.
74. Berglund, G. I., et al., *Purification and characterization of pancreatic elastase from North Atlantic salmon (Salmo salar)*. Mol. Mar. Biol. Biotechnol, 1998. 7(2): p. 105–14.
74. Kunkel T A, Proc. Natl. Acad. Sci., USA, 1985, 82:488–92.
75. Varshney U, van de Sando J H, Nucleic Acids Res., 1989, 17:813.
76. Amann E., Ochs B., Abel K. J., Gene 1988, 69:301–15.

What is claimed is:

1. An isolated enzyme with uracil-DNA glycosylase activity, wherein said enzyme has an amino acid sequence as set forth in SEQ ID NO: 2 from amino acid 82 to amino acid 301, or a biologically functional part thereof having uracil-DNA glycosylase activity.

2. An isolated enzyme having uracil-DNA glycosylase activity comprising the enzyme of claim 1 and a subcellular localization signal attached to the N-terminal, wherein said localization signal is as set forth in SEQ ID NO: 2 from amino acid 1 to amino acid 81.

3. An isolated enzyme having uracil-DNA glycosylase activity comprising the enzyme of claim 1 and a detectable label.

4. A composition for use in preventing experimental carry-over of active glycosylase in a PCR reaction comprising the enzyme according to claim 1.

5. A composition for use in preventing experimental carry-over of active glycosylase in a PCR reaction comprising the enzyme according to claim 2.

6. A composition for use in preventing experimental carry-over of active glycosylase in a PCR reaction comprising the enzyme according to claim 3.

* * * * *